United States Patent
Woolfson et al.

(10) Patent No.: US 9,549,746 B2
(45) Date of Patent: Jan. 24, 2017

(54) DELIVERY DEVICE AND METHOD

(75) Inventors: A. David Woolfson, Belfast (GB);
Desmond Ian John Morrow, Belfast (GB); Anthony Morrissey, Tower Blarney (IE); Ryan F. Donnelly, Newry Co. Down (GB); Paul A. McCarron, Newtownabbey (GB)

(73) Assignee: THE QUEEN'S UNIVERSITY OF BELFAST, Belfast (GB)

( * ) Notice: Subject to any disclaimer, the term of this patent is extended or adjusted under 35 U.S.C. 154(b) by 1297 days.

(21) Appl. No.: 12/680,118

(22) PCT Filed: Sep. 29, 2008

(86) PCT No.: PCT/GB2008/003280
§ 371 (c)(1),
(2), (4) Date: Sep. 16, 2010

(87) PCT Pub. No.: WO2009/040548
PCT Pub. Date: Apr. 2, 2009

(65) Prior Publication Data
US 2010/0256064 A1    Oct. 7, 2010

(30) Foreign Application Priority Data

Sep. 28, 2007 (GB) .................................. 0718996.2
Aug. 28, 2008 (GB) .................................. 0815654.9

(51) Int. Cl.
| | | |
|---|---|---|
| A61K 9/70 | (2006.01) |
| A61M 5/32 | (2006.01) |
| A61M 31/00 | (2006.01) |
| A61B 17/20 | (2006.01) |
| A61M 37/00 | (2006.01) |
| A61F 2/848 | (2013.01) |
| A61K 9/00 | (2006.01) |

(52) U.S. Cl.
CPC ........ *A61B 17/205* (2013.01); *A61M 37/0015* (2013.01); *A61F 2/848* (2013.01); *A61K 9/0021* (2013.01); *A61M 2037/0046* (2013.01)

(58) Field of Classification Search
CPC .................................................. A61M 37/00
USPC ........................................................ 506/13
See application file for complete search history.

(56) References Cited

U.S. PATENT DOCUMENTS

| | | |
|---|---|---|
| 5,439,446 A | 8/1995 | Barry |
| 6,230,051 B1 | 5/2001 | Cormier et al. |
| 6,256,533 B1 | 7/2001 | Yuzhakov et al. |
| 6,379,324 B1 | 4/2002 | Gartstein et al. |
| 6,451,240 B1 | 9/2002 | Sherman et al. |
| 6,565,532 B1 | 5/2003 | Yuzhakov et al. |
| 6,583,225 B1 * | 6/2003 | Plochocka et al. ........... 525/193 |
| 6,591,124 B2 | 7/2003 | Sherman et al. |
| 6,603,987 B2 | 8/2003 | Whitson |
| 6,611,707 B1 | 8/2003 | Prausnitz et al. |
| 6,652,478 B1 | 11/2003 | Gartstein et al. |
| 6,663,820 B2 | 12/2003 | Arias et al. |
| 6,743,211 B1 | 6/2004 | Prausnitz et al. |
| 6,749,792 B2 | 6/2004 | Olson |
| 6,767,341 B2 | 7/2004 | Cho |
| 6,821,281 B2 | 11/2004 | Sherman et al. |
| 6,908,453 B2 | 6/2005 | Fleming et al. |
| 6,924,087 B2 | 8/2005 | Yeshurun et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 7,027,478 B2 | 4/2006 | Ackley |
| 7,108,681 B2 | 9/2006 | Gartstein et al. |
| 7,182,747 B2 | 2/2007 | Kwon |
| 7,211,062 B2 | 5/2007 | Kwon |
| 7,651,946 B2 | 1/2010 | Wilke et al. |
| 2005/0112135 A1 * | 5/2005 | Cormier et al. ........... 424/185.1 |
| 2006/0200069 A1 | 9/2006 | Cormier et al. |
| 2007/0110810 A1 * | 5/2007 | Smith ........................ 424/486 |
| 2009/0182306 A1 | 7/2009 | Lee et al. |

FOREIGN PATENT DOCUMENTS

| | | |
|---|---|---|
| EP | 1517722 A1 | 3/2005 |
| JP | 2007-130417 A | 5/2007 |
| WO | WO-03/072287 A1 | 9/2003 |
| WO | WO-2006/016364 A2 | 2/2006 |
| WO | WO-2007/012114 A1 | 2/2007 |
| WO | WO-2007/040938 A1 | 4/2007 |
| WO | WO-2008/011625 A2 | 1/2008 |

OTHER PUBLICATIONS

Donnelly et al. ("Microneedle-mediated intradermal delivery of 5-aminolevulinic acid: Potential for enhanced topical photodynamic therapy", Journal of Controlled release, 2008, vol. 129, pp. 154-162).*
Lee et al., ("Dissolving microneedles for transdermal drug delivery", Biomaterials, 2008, vol. 29, pp. 2113-2124).*
Sullivan et al., ("Minimally Invasive Protein Delivery with Rapidly Dissolving Polymer Microneedles", Advanced Materials, 2008, vol. 20, pp. 933-938).*
McCarron et al., (Journal of Polymer Science, 2004, vol. 91, 1576-1589).*
McCarron, Paul A., et al., "Influence of Plasticizer Type and Storage Conditions on Properties of Poly(methyl vinyl ether-co-maleic anhydride) Bioadhesive Films", Journal of Applied Polymer Science, vol. 91, 1576-1589 (2004).
Ito, Yukako, et al., "Feasibility of microneedles for percutaneous absorption of insulin", European Journal of Pharmaceutical Sciences 29 (2006) 82-88.
Ito, Yukako, et al., "Self-dissolving microneedles for the percutaneous absorption of EPO in mice", Journal of Drug Targeting, Jun. 2006; 14(5): 255-261.
Türkavci, Levent, "International Search Report", for PCT/GB2008/003280 as mailed Feb. 20, 2009, 5 pages.

* cited by examiner

*Primary Examiner* — Jeffrey T Palenik
(74) *Attorney, Agent, or Firm* — Winstead PC

(57) ABSTRACT

A microprotrusion array for use in transport of a material across a biological barrier, wherein said array comprises a plurality of microprotusions composed of a swellable polymer composition.

16 Claims, 15 Drawing Sheets

| Polymeric Films | Prepared from aqueous gels of concentration: |
|---|---|
| Amylopectin | 25% w/w |
| carboxymethyl cellulose, (CMC) | 26.5% w/w |
| Poly(HEMA) | - |
| polyvinyl alcohol (PVA) | 30% w/w |
| Hydroxy ethylcellulose, (HEC) | 5% w/w |

FIG. 16

| Time | Amylopectin | CMC | Poly(HEMA) | PVA | HEC |
|---|---|---|---|---|---|
| 15 | 17.08 | 23.24 | 11.82 | 62.67 | ND |
| 30 | 20.77 | ND | 20.18 | 82.11 | ND |
| 60 | 37.79 | ND | 37.54 | 154.53 | ND |
| 180 | 61.05 | ND | 40.67 | 309.51 | ND |
| 240 | ND | ND | 41.79 | 351.55 | ND |
| 1440 | ND | ND | 46.22 | 445.68 | ND |

ND – Not determined, because these films dissolved over time.
HEC films broke into pieces within 15.0 min.

FIG. 17

| Time | PMVE/MA 10%:PEG 10,000 | PMVE/MA 15%:PEG 10,000 | PMVE/MA 20%:PEG 10,000 |
|---|---|---|---|
| 15 | 242.33 | 92.19 | 52.53 |
| 30 | 519.71 | 169.71 | 90.16 |
| 60 | 971.26 | 412.87 | 251.87 |
| 180 | 1269.59 | 1002.34 | 982.15 |
| 240 | 1272.14 | 1124.56 | 1013.53 |
| 1440 | 1272.14 | 1242.67 | 1039.22 |

FIG. 18

| Films | Force to break (N) |
|---|---|
| Amylopectin | ND* |
| CMC | 77 |
| Poly(HEMA) | 4 |
| PVA | ND** |
| HEC | ND** |
| PMVE/MA 10%:PEG 10,000 | 6.9 |
| PMVE/MA 15%:PEG 10,000 | 16.29 |
| PMVE/MA 20%:PEG 10,000 | 36.77 |

*Film was very brittle
**Films were very flexible in nature

FIG. 19

| Material used | % reduction in microprojection height |
|---|---|
| PMVE/MA 20%:PEG 10,000 | 13.54 |
| PMVE/MA 15%:PEG 10,000 | 14.73 |
| PMVE/MA 10%:PEG 10,000 | 12.35 |
| Amylopectin | 39.29 |
| CMC | 28.57 |
| HEC | 21.43 |
| Poly(HEMA) | 17.86 |
| PVA | 28.57 |

A) Amylopectin

B) CMC

C) HEC

FIG. 20 Contd.
D) pHEMA
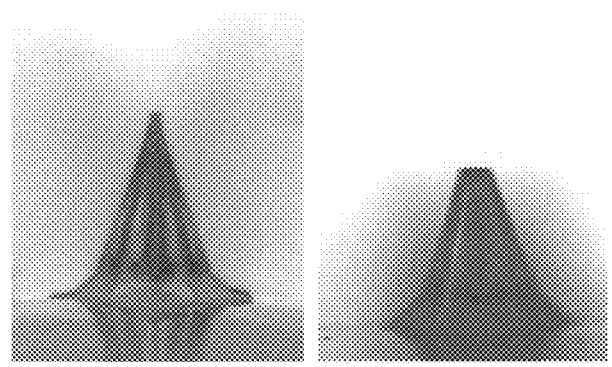
E) PVA
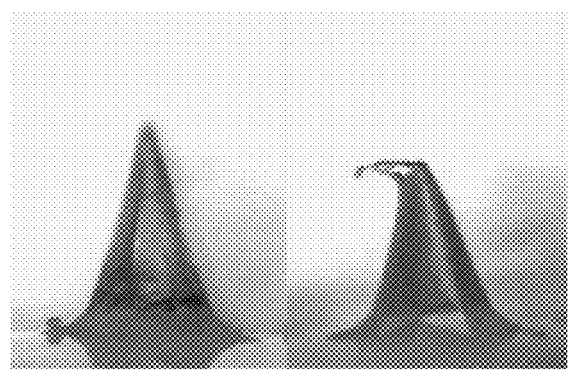
F) PMVE/MA 20%:PEG 10,000
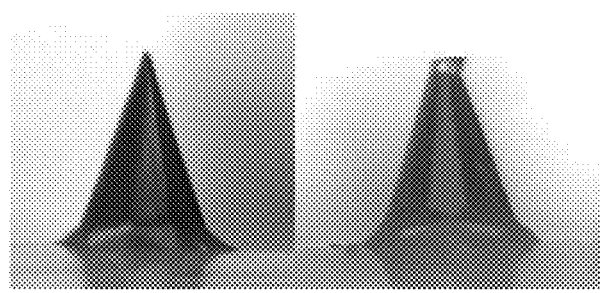

DELIVERY DEVICE AND METHOD

FIELD OF THE INVENTION

This invention relates to transdermal delivery means, in particular, microprotrusion-based devices for the delivery of beneficial substances across or into the skin, or for the monitoring of levels of substances of diagnostic interest in the body.

BACKGROUND TO THE INVENTION

Drug Delivery

The worldwide transdermal patch market for the delivery of drug substances into or through the skin approaches $4 billion, yet is based on only a small number of drugs. The limitations on the number of drugs which are routinely administered transdermally is largely a consequence of the outermost 10-15 μm (in the dry state) of tissue, the stratum corneum (SC). The SC thus constitutes the main barrier to exogenous substances, including drugs. Before being taken up by blood vessels in the upper dermis and prior to entering the systemic circulation, substances permeating the skin must diffuse through the highly organised intercellular lipid bilayers of the SC. This intercellular microroute, which is lipophilic, is the primary pathway for exogenous substances to pass through the SC barrier by passive diffusion along a concentration gradient between delivery vehicle and the SC. The ideal properties of a molecule capable of effective passive diffusion and, thus, penetration through the SC barrier are known to be:

1. Molecular mass less than 600 Da
2. Adequate solubility in both oil and water so that the membrane concentration gradient, which is the driving force for passive drug diffusion along a concentration gradient, may be high
3. Partition coefficient such that the drug can diffuse out of the vehicle, partition into, and move across the SC, without becoming sequestered within it
4. Low melting point, correlating with good solubility, as predicted by ideal solubility theory.

Drug molecules that suffer poor oral bioavailability or susceptibility to first-pass metabolism, and are thus often ideal candidates for transdermal delivery, often fail to realise their clinical application because they do not meet one or more of the above conditions. Macromolecular drugs such as peptides, proteins and nucleic acid fragments are precluded from successful transdermal administration, not only by their large sizes, but also by their extreme hydrophilicities. Drugs with substantial aqueous solubilities, for example, water-soluble salts of drug substances with acidic or basic moieties, are precluded from successful transdermal administration by their inability to cross the lipophilic intercellular microroute through the SC barrier.

Several approaches have been used to enhance the transport of drugs through the SC. However, in many cases, only moderate success has been achieved and each approach is associated with significant problems.

Chemical penetration enhancers allow only a modest improvement in penetration. Chemical modification of the penetrant to increase lipophilicity is not always possible and, in any case, necessitates additional studies for regulatory approval, due to generation of new chemical entities. Significant enhancement in delivery of a large number of drugs has been reported using iontophoresis. However, specialized devices are required and the agents delivered tend to accumulate in the skin appendages. The method is presently best-suited to acute applications. Electroporation and sonophoresis are known to increase transdermal delivery. However, they may both cause pain and local skin reactions and sonophoresis may cause breakdown of the therapeutic entity. Techniques aimed at removing the SC barrier, such as tape-stripping and suction/laser/thermal ablation are impractical, while needle-free injections have so far failed to replace conventional needle-based delivery, for example of insulin. Clearly, a robust alternative strategy is required to enhance drug transport across the SC and thus widen the range of drug substances amenable to transdermal delivery.

Minimally Invasive Monitoring

Minimally-invasive monitoring, whereby blood concentrations of drugs and analytes, such as glucose and drug substances, can be indirectly assessed without recourse to direct blood sampling, produces less pain, inconvenience and risk of infection for patients and saves clinician and nursing time. However, the stratum corneum has evolved into an exquisite, almost impermeable, barrier to outward migration of blood constituents. The small amounts of sweat and sebum produced under normal conditions mean that their collection and analysis is not practical. In any case, their composition does not, in most instances, accurately reflect blood concentration of analytes of interest. In minimally-invasive monitoring, interstitial fluid in the skin is extracted and used to accurately estimate blood analyte concentrations. The technique is fraught with difficulties, though, and often requires very specialized equipment. Given that sales of conventional finger-prick analysis devices for direct monitoring of blood glucose alone total $2 billion per annum, advancements in this field would be clinically desirable.

The concept of using a microstructured device consisting of a plurality of microprotrusions to breach the stratum corneum barrier was first proposed in the 1970s. Various devices comprising solid microprotrusions have been developed to produce a system that will puncture the stratum corneum leaving microscopic holes and that will enable subsequent inward drug delivery or outward migration of interstitial fluid. The production of solid microprotrusions and microneedle arrays using for example silicon have been described in the art, for example see U.S. Pat. Nos. 6,743,211, 6,743,211, 6,743,211, IE 2005/0825, U.S. Pat. Nos. 60/749,086, 6,924,087, 6,743,211, 6,663,820, 6,743,211, 6,767,341, 6,743,211, 6,663,820, 6,652,478, 6,743,211, 6,749,792, 6,451,240, 6,767,341, 6,743,211, 6,230,051, 6,908,453, 7,108,681, 6,931,277, EP1517722B1, US20060200069A1, U.S. Pat. Nos. 6,611,707, 6,565,532, 6,960,193, 6,743,211, 6,379,324, WO2007/040938A1, U.S. Pat. Nos. 6,256,533, 6,743,211, 6,591,124, 7,027,478, 6,603,987, 6,821,281, and 6,565,532.

A method for preparing solid microprotrusions from dextrin, chondroitin and albumin has been disclosed by Kyoto Pharmaceutical University (Ito et al, J Drug Target 14 (5): 255-261 2006; Ito et al, Eur J Pharm Sci 29: 82-88 2006). This "thread forming" method involves spreading a solution containing a known "thread-forming" material on a flat surface. The solution then has its surface contacted by a projection, which is moved upwards quickly, forming a series of polymer "threads", which then dry to form microprotrusions. However, microprotrusions prepared from molten carbohydrate materials (eg dextrin, maltose) are extremely hygroscopic and rapidly absorb moisture under ambient conditions, losing their shape and becoming soft and extremely adhesive. Carbohydrate-based microprojections, upon skin puncture, rapidly form an adhesive matrix that blocks the formed holes, preventing appreciable drug delivery. Furthermore, drug loss is associated with such microprotrusion manufacture, as the drug substance needs to be heated to high temperatures required to melt such carbohydrate materials.

However, despite the considerable published work in the area of microprotrusions, it is particularly noteworthy that no microprotrusion-based products are presently marketed for the delivery of beneficial substances into or through the skin, or for the monitoring of levels of substances of diagnostic interest in the body. This is because the use of such systems presently known in the art is associated with a number of significant problems for these purposes, namely:

1 Production of microprotrusions by most previously patented methods is expensive;
2 Elemental silicon, widely used as the material for microprotrusions, is not an FDA-approved biomaterial & broken silicon or metal microprotrusions could cause skin problems—This is a particular problem for the notoriously brittle microprojections produced by dry etching of silicon;
3 Solid, non-coated needles require a two-step application process, which is undesirable;
4 Accurately coating microprotrusions is difficult and these coated microprotrusions subsequently only deliver a very small amount of drug as a bolus;
5 Preliminary experiments, conducted in our laboratory using human volunteers (n=5), showed transepidermal water loss (TEWL), a measure used worldwide as an indication of stratum corneum permeability, increased to approximately 30 g m$^{-2}$ h$^{-1}$ immediately upon microprotrusion puncture, but had returned to background (10 g m$^{-2}$ h$^{-1}$) within about 5 minutes;
6 Hollow microprotrusions have only one outlet and can become blocked by compressed dermal tissue;
7 Biomolecules can be significantly degraded by the heating used to produce polymeric microprotrusions from molten polymers or carbohydrates; and
8 The strength of carbohydrate and polymeric microprotrusions may be significantly compromised by incorporation of drug substances.

Thus the use of conventional microprotrusion based devices is associated with a great number of problems.

SUMMARY OF THE INVENTION

Surprisingly, the present inventors have found that particular polymers which swell in the presence of water have sufficient mechanical strength to function as microprotrusions that can puncture the stratum corneum barrier. This surprising finding allows the provision of microprotrusion arrays of swellable polymers for use in methods of bypassing the stratum corneum barrier and allowing successful delivery of beneficial substances across or into the skin.

Thus, in a first aspect of the present invention, there is provided a microprotrusion array for use in transport of a material across a biological barrier, wherein said array comprises a base element and a plurality of microprotrusions which project from said base element, wherein the microprotrusions are composed of a swellable hydrogel forming polymer composition.

Any hydrogel polymer composition which can penetrate the stratum corneum of skin and which swells in the presence of liquid may be used in the present invention.

In one embodiment, the microprotrusions of the array of and for use in the invention are fabricated from one or more hydrogel-forming polymers containing one or more hydrophilic functional groups. Examples of suitable polymers include, but are not necessarily limited to, poly(vinyl alcohol), amylopectin, carboxymethylcellulose (CMC) chitosan, poly(hydroxyethylmethacrylate) (polyHEMA), poly(acrylic acid), and poly(caprolactone), or a Gantrez®-type polymer. Gantrez®-type polymers include poly(methylvinylether/maleic acid), esters thereof and similar, related, polymers (eg poly(methyl/vinyl ether/maleic anhydride).

In a particular embodiment of the invention, the hydrogel-forming polymer is a Gantrez®-type polymer such as poly (methyl/vinyl ether/maleic acid) (PMVEMA), an ester thereof or poly(methyl/vinyl ether/maleic anhydride) (PMVEMAH).

Crosslinking of polymers may be used to further vary the strength and swelling characteristics of microprotrusions as well as the release characteristics of the microprotrusions for delivery of an active agent. For example a lightly-crosslinked hydrogel microprotrusion could rapidly deliver a drug bolus where one dose only is required e.g. for vaccine delivery. Optionally, a moderately-crosslinked hydrogel microprotrusion could be used to allow prolonged drug delivery, thus facilitating a constant drug plasma level. Optionally moderately-crosslinked hydrogel microprotrusions could keep puncture holes in the SC open. Indeed, moderately-crosslinked hydrogel microprotrusions might optionally widen the puncture holes as a result of absorption of moisture from tissue, and swelling of the microprotrusions.

The polymer composition of the microprotrusions and/or the base element may be cross-linked using any suitable technique known in the art. The crosslinking may be physical or chemical or a combination of both. Suitable cross-linking agents include polyhydric alcohols (eg glycerol, propylene glycol (poly(ethylene glycol) or a polyamino compound which can form amides with reactive groups of a polymer.

In one embodiment, of the invention, the hydrogel-forming polymer is a Gantrez® type polymer cross-linked using a polyhydric alcohol.

The microprotrusions of the microprotrusion arrays of the invention may be of any size and shape such that they can penetrate the stratum corneum of mammalian skin without breaking upon their insertion into the skin.

In one embodiment, the microprotrusions of the microprotrusion arrays of the invention are 1-3000 μm in height. In one embodiment, the microprotrusions have a width (or, in the case of microprotrusions with substantially circular cross sections, a diameter) of 50-500 μm.

The base element and microprotrusions may be comprised of the same or different materials.

Typically the base element will be composed of the same polymer composition as the microprotrusions.

The mechanical strength and rate of swelling of the microprotrusions of the microprotrusion arrays of the invention will be determined by a number of factors including the shape of the microprotrusions and the polymer(s) of which the microprotrusions are composed.

The microprotrusion arrays of the invention may be used for many different purposes. In one embodiment, they are for use in the transdermal delivery of an active agent, for example a beneficial substance, such as a drug, to the skin.

Accordingly, in a second aspect of the invention, there is provided a transdermal delivery device comprising a microprotrusion array according to the first aspect of the invention.

In such transdermal delivery devices, an active agent may be comprised within a reservoir or matrix with which the microprotrusion array is in communication. In use, on insertion of the microprotrusion array into skin, the active agent moves from the reservoir or matrix through the microprotrusions to the skin.

Additionally or alternatively, the active agent may be comprised within the polymer composition of the microprotrusion array. This has the distinct advantage over conventional microneedle arrays in which drugs are delivered via a channel in the microneedle that, on insertion into the skin, drug delivery may be initiated almost immediately.

In particular embodiments, the active agent(s) can be chemically bonded to the polymer(s) making up the microprotrusions and/or base elements. In this case, the active agent can be released upon insertion into the skin by; dissolution of the microprotrusions, hydrolysis, enzymatic or spontaneous non-catalysed breakage of the bonds holding it to the polymer(s). The rate of drug release can thus be determined by the rate of reaction/bond breakage.

In embodiments of the transdermal delivery device of the invention, movement of an active agent from the microprotrusion array into the skin may occur passively. Alternatively, movement may be controlled externally, for example iontophoretically. Thus in a third aspect of the present invention, there is provided an iontophoretic device comprising a microprotrusion array of the first aspect of the invention.

In a fourth aspect of the present invention, there is provided a method of delivering an active agent through or into the skin comprising
  providing a microprotrusion array according to the first aspect of the invention or a transdermal therapeutic device according to the second aspect of the invention, wherein the microprotrusion array or transdermal therapeutic device comprises said agent,
  applying the microprotrusion array to the skin such that the microprotrusions protrude through or into the stratum corneum,
  allowing the microprotrusions to swell,
  allowing the active agent to flow through the microprotusions into the skin.

Transdermal delivery devices of and for use in the invention can be affixed to the skin or other tissue to deliver active agents continuously or intermittently, for example for durations ranging from a few seconds to several hours or days.

Arrays of and for use in the invention may comprise groups of microprotrusions having different characteristics from each other, for example having different shapes, polymer compositions, crosslinkers or degrees of crosslinking, thus enabling a single microprotrusion array to have regions which can deliver active agents, e.g. drugs at different rates. This would enable, for example, a rapid bolus to be delivered to a patient on positioning of the microprotrusion array followed by a slower sustained release of the same active agent. Indeed, the microprotrusion arrays of the invention may be used to deliver more than one active agent from the same transdermal therapeutic device. For example, a first active agent could be comprised within the polymer of which the microprotrusions are composed with a second active agent stored in a reservoir. On positioning on the skin and puncturing of the stratum corneum, the microprotrusions will swell and the active agent will be released from the microprotrusions. Subsequently, the second active agent may be released from the reservoir and enter the skin via the microprotrusions.

Drug contained in the microprotrusions themselves will be rapidly released upon swelling, initially as a burst release due to drug at the surface of the microprotrusions. The subsequent extent of release will be determined by crosslink density and the physicochemical properties of the drug. Release of drug from the drug reservoir will occur more slowly at first as a result of the time required to swell the microprotrusions up as far as the drug reservoir, subsequent partitioning of the drug into the swollen microprotrusions and diffusion of the drug through the swollen matrix. The microarrays may thus be adapted to deliver two active agents in succession, with the composition adapted, e.g. by crosslinking of the composition of the microprotrusions, to vary delivery times of one or both active agents.

Active agents which may be delivered through the stratum corneum using the microprotrusion arrays of the invention include drugs, nutrients or cosmetic agents.

As well as being suitable for use in transdermal delivery devices, the microprotrusion arrays of the invention can be utilised to transfer substances across the skin in the reverse direction, for example to facilitate the monitoring of levels of substances of diagnostic interest in the body and for the sampling of substances from the skin.

Accordingly, in a fifth aspect of the present invention, there is provided a method of sampling for an analyte in the skin interstitial fluid, said method comprising the steps of:
  a. providing a microprotrusion array of the first aspect of the invention,
  b. applying the microprotrusion array to the skin such that the microprotrusions protrude through the stratum corneum,
  c. allowing the microprotrusions to swell,
  d. allowing an analyte to flow from the skin through the microprotusions to a collection chamber;
  e. detecting the presence of said analyte in said collection chamber.

Sampling using microprotrusion arrays of the invention may be performed passively, or, in alternative embodiments, actively, for example via reverse iontophoresis.

According to a sixth aspect of the invention there is provided a method of treatment comprising the step of providing a drug to a subject in need thereof via a microprotrusion array according to the first aspect of the invention, a transdermal delivery device according to the second aspect of the invention or an iontophoretic device according to the third aspect of the invention.

The present invention also provides the use of a microprotrusion array according to the first aspect of the invention, a transdermal delivery device according to the second aspect of the invention or an iontophoretic device according to the third aspect of the invention for the administration of an active agent to the skin of a subject in need thereof.

The microprotrusion arrays of the invention may also be used for delivery of membrane-impermeable molecules into cells, applications in molecular biology, drug delivery into neural tissue and other tissues, for example, delivery into the skin, e.g. or for a local therapeutic effect, or for intravessel delivery, e.g. for penetration and subsequent delivery of an antirestenosis agent into atherosclerotic arteries. Such applications also include uses as functional (sensing, delivery of therapeutic active agents) surfaces on medical devices, for example on catheters and stents which could be used to penetrate tissue and deliver a beneficial substance upon swelling.

Indeed, in a particular embodiment, microprotrusion arrays of the invention may be used for the delivery of an active agent to a body lumen via an intravessel delivery device, for example a catheter or a stent.

Accordingly, in a seventh aspect of the present invention, there is provided an intravessel delivery device comprising one or more microprotrusion arrays according to the first aspect of the present invention.

The intravessel delivery device may be any device suitable for delivery of agents to body lumens, such as arteries, veins, other tubular structures such as the urethra etc. The intravessel delivery device may be or comprise, for example, a catheter or stent.

The intravessel delivery device may be provided with any suitable support means for delivery of the microprotrusion array to the target lumenal surface such as the endothelial surface of a particular blood vessel, in which it is to be positioned in use, and/or for bringing it into contact with the target surface.

For example, suitably, in order to prevent damage to the array(s) during delivery through the lumen of e.g. blood vessels to an intended site of use, and indeed to prevent damage to the vessels through which the intravessel delivery device is delivered, the array(s) may be provided on support means which, during insertion of the intravessel delivery device to its desired position, maintains the array(s) in a position such that minimal or no contact occurs between the array(s) and the lumenal surfaces through which the intravessel delivery device is passed. Preferably, once positioned correctly, for example in a target blood vessel, the support means may be manipulated to bring the array(s) into contact with the desired lumenal surface.

Any suitable support means for achieving this may be used. For example, the support means may be a conventional stent, which can be expanded from a closed position in which the stent has a first diameter to an open position in which the diameter of the stent is greater. Any suitable means conventionally used to position stents may be used or adapted to deliver the microprotrusion arrays. For example, the arrays may be positioned on a closed support means which when in position is opened i.e. expanded circumferentially, e.g. by means of inflation of an angioplasty balloon inside the closed support means. Once the arrays have been positioned on the desired lumenal surface, the ballon may be deflated and withdrawn.

As noted above the support means may comprise any suitable structure, for example those used in stents and stent delivery. For example, the support means may have one or more of a collapsible metal frame, supporting wires or springs.

To prevent damage to vessels and/or arrays during delivery, the arrays may be maintained within cover means, e.g. a protective sheath, which on delivery of the intravessel delivery means to the target vessel is withdrawn in order that the arrays may be brought into contact with the target vessel wall.

In one embodiment, the arrays may be positioned on a support means, which, on withdrawal of the positioning means and/or intravessel delivery device, remains in position within the vessel to provide a supporting function to the vessel as with conventional stents. Stents currently in use are often used to help to support the wall of a blood vessel during balloon angioplasty such that the stent can be manoeuvred into place within the vessel and expanded. Intravessel delivery device of such embodiments of the present invention have the advantage over conventional stents of not only providing support to a vessel via the device, but further enabling localised delivery of therapeutic active agents through the walls of such blood vessels.

In an alternative embodiment, the microprotrusion array support means, while remaining in position once the delivery means are withdrawn, does not provide a supporting function to the vessel itself. In a further embodiment, on withdrawal of the intravessel delivery device after positioning of the arrays, any support means are also withdrawn. In such embodiments, the arrays may be left in situ, the microprotrusions in effect anchoring the arrays in the walls of the vessel.

The microprotrusion arrays may be arranged on the intravessel delivery device or support means thereof in any suitable configuration. For example, the microprotrusion array may be provided as a slab-type array configuration. In such a configuration, the base of the array is preferably flexible to some extent to enable manipulation of the microprotrusions across the array into contact with a vessel wall in use.

In an alternative embodiment, the microprotrusion arrays may be provided in strips comprising a single row of two or more microprotrusions. Such strips may be rigid.

In use, the support means help to position the microprotrusion array strip(s) or slabs to pierce the vessel lining of the blood vessel.

Each intravessel delivery device may comprise one or more microprotrusion arrays arranged in strips or slabs or mixtures thereof. The arrays may be arranged substantially equidistantly around the delivery device or, alternatively, concentrated one or more localised areas, e.g. quadrants, of the outer surface of such a delivery device.

The intravessel delivery device of the present invention may be used for delivery of substances, such as drugs through the lumenal wall of any body vessel. In one embodiment, the stent is for use in the transendothelial delivery of an active agent in a blood vessel, for treatment in cardiovascular disease.

In an eighth aspect of the present invention, there is provided a method of delivering an active agent by penetrating a tissue comprising;
  providing an intravessel delivery device according to the seventh aspect of the present invention;
    introducing the intravessel delivery device to a target vessel
    bringing microprotrusion array into contact with the vessel wall tissue such that the microprotrusions protrude through or into the vessel wall; and
    allowing the active agent to flow through the microprotusions through or into the vessel wall.

In a ninth aspect of the present invention, there is provided a method of treatment comprising the step of administering an active agent to a subject in need thereof via an intravessel delivery device according to the seventh aspect of the present invention.

Preferred features of each aspect of the invention are as for each of the other aspects mutatis mutandis unless the context demands otherwise.

DETAILED DESCRIPTION

As demonstrated below, the present inventors have shown that microprotrusion arrays in which the microprotrusions are composed of swellable polymers can puncture the stratum corneum of mammalian skin without breaking upon insertion into the skin and can be used for efficient delivery of active substances through the stratum corneum without many of the problems associated with the use of conventional solid microneedles.

For example, FDA-approved hydrogel materials can be utilised to form the microprotrusion and such hydrogel materials can be inexpensive and biocompatible. The drug dose which can be provided by a microprotrusion may not limited by how much can be loaded into a microprotrusion, as the drug could be contained in an attached drug reservoir attached to the upper surface of the microprotrusion array.

The swelling of the microprotrusions on entry to the skin has a number of advantages over conventional microneedle arrays or indeed sugar microneedles. For example, where the microprotrusion array is used for drug delivery, the increased surface area of microprotrusion in contact with the epidermal layer underneath the stratum corneum resulting from the swelling of the microprotrusions enables enhanced delivery of drug to the epidermal layer underneath the stratum corneum. In particular embodiments arrays of swellable polymeric microprotrusions can absorb moisture upon insertion into the skin and swell to form continuous aqueous channels between the external environment and the dermal microcirculation, thus forming an 'aqueous bridge' across the lipophilic stratum corneum barrier. Such channels do not have the tendency to block on positioning of the array, in contrast to conventional silicon based microneedle devices having channels therein. Optionally, the microprotrusions can release drug from every point on the surface of the microprotrusion further minimising blockage of the microprotrusion by tissue. Optionally a hydrogel microprotrusion array could be integrated with a drug reservoir to give a rapid bolus dose, achieving a therapeutic plasma level, followed by controlled, prolonged delivery to maintain this level. Optionally, swollen hydrogel materials can contain >70%, for example >80%, such as >90% water. By having a high water content, drug diffusion is facilitated, as there will be less chance of impedance of drug movement due to collision with polymer chains. In addition, water allows passage of ions and polar substances and facilitates electroosmotic flow under a potential gradient. Thus, conduction of charged and/or polar substances and fluid moving by electro-osmotic flow is possible.

Swellable Polymers

Microprotrusions can be fabricated from any suitable swellable polymer, which in its dry state is hard and brittle to allow penetration of the stratum corneum, but then which, upon taking up moisture swells to allow diffusion of therapeutic active agents. For example, the microprotrusions may be composed of one or more of a number of polymers known to form hydrogels including, but not limited to, the following; poly(vinyl alcohol), poly(hydroxyethylmethacrylate), poly(methylvinylether/maleic acid), poly(acrylic acid), poly (caprolactone).

In particular embodiments, the polymers of the microprotrusions are crosslinked, either physically, chemically or both. The microprotrusion array can comprise groups of microprotrusions wherein a first group comprises at least one different cross-linker to at least a second group.

In particular embodiments the microprotrusions may not be crosslinked and will dissolve following an initial swelling phase upon puncturing the stratum corneum and coming into contact with skin moisture. In this case, the therapeutic active agents can be released into the skin at a rate determined by the rate of dissolution of the microprotrusions. The rate of dissolution of particular microprotrusions is dependent on their physicochemical properties which can be tailored to suit a given application or desired rate of drug release.

Combinations of non-crosslinked, lightly crosslinked and extensively crosslinked microprotrusions can be combined in a single device so as to deliver a bolus dose of an active agent e.g. or therapeutic substance(s), achieving a therapeutic plasma level, followed by controlled delivery to maintain this level. This strategy can be successfully employed whether the therapeutic substance is contained in the microprotrusions and base element or in an attached reservoir.

In further embodiments, the base element and microprotrusions may contain in their matrix, defined quantities of one or more water soluble excipients. Upon insertion into skin these excipients will dissolve leaving pores behind in the matrix of the base element and microprotrusions. This can enhance the rate of release, which can be further controlled by changing the excipient, its concentration and/or its particle size. Suitable excipients include, but are not limited to glucose, dextrose, dextran sulfate, sodium chloride and potassium chloride or other water soluble excipients known in the art.

As noted above, in order to be of use in transdermal delivery or to monitor levels of substances in the body, arrays of microprotrusions must be capable of creating openings in the stratum corneum barrier through which beneficial substances can move. Thus, the force of insertion is less than the force required to fracture the microprotrusions.

Suitably, the microprotrusions do not fracture when a pressure of insertion of less than 5.0 N $cm^{-2}$, for example less than 3.0 N $cm^{-2}$, such as less than 0.5 N $cm^{-2}$ is exerted on the microprotrusions along their length.

A microprotrusion can be any suitable size and shape for use in an array to puncture the stratum corneum. The microprotrusions of the array of the first aspect of the present invention are designed to pierce and optionally cross the stratum corneum. Suitably, the height of the microprotrusions can be altered so as to allow penetration into the upper epidermis, as far as the deep epidermis or even the upper dermis, but not allowing penetration deep enough into the skin to cause bleeding. In one embodiment, the microprotrusions are conical in shape with a circular base which tapers to a point at a height of the microprotrusion above the base.

In embodiments of the microprotrusion array the microprotrusions can be in the range of 1 μm to 3000 μm in height. For example, the microprotrusions can have heights in the range 50 μm to 400 μm, for example 50 to 100 μm. Suitably, in embodiments of the arrays of the invention, microprotrusions can have a width, e.g. diamater in the case of microprotrusions of circular cross-section diameter of 1-500 μm at their base. In one embodiment microprotrusions of and for use in the invention can have a diameter in the range 50-300 μm, for example 100-200 μm. In another embodiment, the microprotrusion of the invention may be of a diameter in the range of 1 μm to 50 μm, for example in the range 20-50 μm.

The apical separation distance between each of the individual microprotusions in an array can be modified to ensure penetration of the skin while having a sufficiently small separation distance to provide high transdermal transport rates. In embodiments of the device the range of apical separation distances between microprotrusions can be in the in the range 50-1000 μm, such as 100-300 μm, for example 100-200 μm. This allows a compromise to be achieved between efficient penetration of the stratum corneum and enhanced delivery of therapeutic active agents or passage of interstitial fluid or components thereof.

It will be apparent to those skilled in the art that the microprotrusions of the invention can take any reasonable shape, including, but not limited to, microneedles, cones, rods and/or pillars. As such, the microprotrusions may have the same diameter at the tip as at the base or may taper in diameter in the direction base to tip. The microprotrusions may have at least one sharp edge and may be sharp at the tips. The microprotrusions may be solid, have a hollow bore down at least one longitudinal axis at an angle to the base element and extending to the first side of the base element, they may be porous, or may have at least one channel running down at least one outer surface from tip to base element.

In use, the microprotrusions may be inserted into the skin by gentle applied pressure or by using a specially-designed mechanical applicator applying a pre-defined force. An additional device may be used to reduce the elasticity of skin by stretching, pinching or pulling the surface of the skin so as to facilitate insertion of the microprotrusions. This latter function could be usefully combined with the function of the applicator to produce a single integrated device for insertion of a microprotrusion array.

A number of applicators for microneedle based delivery are known in the art. For example, US20046743211 describes methods and devices for limiting the elasticity of skin by means of stretching, pulling or pinching the skin, so as to present a more rigid, less deformable surface in the area to which microneedle-array-based transdermal drug delivery systems are applied. US 20060200069 describes a spring-loaded impact applicator for the application of coated microprojection arrays to the skin. A further application known in the art is the Alza Macroflux® device which is applied to skin using a specially-designed spring-loaded applicator (Alza Corporation, 2007).

Methods of Manufacture

Microprotrusions composed of polymers known to form hydrogels can be manufactured by any such methods known in the art. For example, they can be prepared by a micromoulding technique using a master template, such as a microprotrusion array made from one or more of a wide variety of materials, including for example, but not limited to; silicon, metal polymeric material. Master templates can be prepared by a number of methods, including, but not limited to, electrochemical etching, deep plasma etching of silicon, electroplating, wet etch processes, micromoulding, microembossing, "thread-forming" methods and by the use of repetitive sequential deposition and selective x-ray irradiation of radiosensitive polymers to yield solid microprotrusion arrays.

Micromoulds can be prepared by coating the master template with a liquid monomer or polymer which is then cured and the master template removed to leave a mould containing the detail of the master template. In the micromoulding technique, a liquid monomer, with or without initiator and/or crosslinking agent is placed in the mould, which is filled by means of gravitational flow, application of vacuum or centrifugal forces, by application of pressure or by injection moulding. The monomer may then be cured in the mould by means of heat or application of irradiation (for example, light, UV radiation, x-rays) and the formed microprotrusion array, which is an exact replicate of the master template is removed. Alternatively, a solution of a polymer with or without crosslinking agent can be placed in the mould, which is filled by means of gravitational flow, application of vacuum or centrifugal forces, by application of pressure or by injection moulding. The solvent can then be evaporated to leave behind a dried microprotrusion array, which is an exact replicate of the master template, and can then be removed from the mould. The solvents that can be used include, but are not limited to, water, acetone, dichloromethane, ether, diethylether, ethyl acetate. Other suitable solvents will be obvious to one skilled in the art. Micromoulds can also be produced without the need for master templates by, for example, micromachining methods and also other methods that will be obvious to those skilled in the art.

For example, in one embodiment, the microprotrusion arrays may be prepared using micromoulds prepared using a method in which the shape of the desired microprotrusions are drilled into a suitable mould material, for example using a laser and the moulds are then filled using techniques known in the art or as described herein.

Microprotrusions composed of polymers known to form hydrogels can also be manufactured using a "self-moulding" method. In this method, the polymeric material is first made into a thin film using techniques well known in the art, including for example, but not limited to, casting, extrusion and moulding. The material may, or may not be crosslinked before the "self moulding" process. In this process, the thin film is placed on a previously-prepared microprotrusion array and heated. Plastic deformation due to gravity causes the polymeric film to deform and, upon hardening, create the desired microprojection structure.

Microprotrusions with a hollow bore can be manufactured by using moulds prepared from hollow master templates or suitably altering the micromachining methods or other methods used to prepare solid microprotrusions. Hollow bores can also be drilled mechanically or by laser into formed microprotrusions. Microprotrusions which have at least one channel running down at least one outer surface from tip to base element can also be produced by suitable modification of the method used to prepare solid microprotrusions. Such alterations will be obvious to those skilled in the art. Channels can also be drilled mechanically or by laser into formed microprotrusions.

Microprotrusions composed of polymers known to form hydrogels can also be manufactured using a "thread forming" method whereby a polymer solution spread on a flat surface has its surface contacted by a projection which is then moved upwards quickly forming a series of polymer "threads", which then dry to form microprotrusions.

In all of the above methods, substances to be incorporated into the microprotrusions themselves (e.g., active therapeutic agents, pore forming agents, enzymes etc.) can be added into the liquid monomer or polymer solution during the manufacturing process. Alternatively, such substances can be imbibed from their solution state in a solution used to swell the formed microprotrusion arrays and dried thereafter or the formed arrays can be dipped into a solution containing the agent of interest or sprayed with a solution containing the agent of interest. Solvents used to make these solutions include water, acetone, dichloromethane, ether, diethylether, ethyl acetate. Other suitable solvents will be obvious to those skilled in the art, as will the processes used to dry the microprotrusion arrays. If the microprotrusions and/or base elements are to be made adhesive, the formed arrays can be dipped into a solution containing an adhesive agent or sprayed with a solution containing an adhesive agent. The adhesive agents used can be a pressure sensitive adhesive or a bioadhesive. These substances are well known and will be obvious to those skilled in the art.

The base element on which the microprotrusions are formed can be varied in thickness by suitable modification of the method of manufacture, including, for example, but not limited to increasing the quantity of liquid monomer or polymer solution used in the manufacturing process. In this way the barrier to diffusion/transport of therapeutic active agents and/or analytes of interest can be controlled so as to achieve, for example rapid delivery or sampling or sustained release. Where therapeutic active agent(s) is/are to be contained within the matrix of the microprotrusions and base element, the thickness of the base element can usefully be increased so as it functions as a fully integrated reservoir.

Cross Linking

Crosslinks may be physical or chemical and intermolecular or intramolecular. Methods for crosslinking polymers are well known in the art. Crosslinking is the process whereby adjacent polymer chains, or adjacent sections of the same polymer chain, are linked together, preventing movement away from each other. Physical crosslinking occurs due to entanglements or other physical interaction. With chemical crosslinking, functional groups are reacted to yield chemical bonds. Such bonds can be directly between functional groups on the polymer chains or a crosslinking agent can be used to link the chains together. Such an agent must possess at least two functional groups capable of reacting with groups on the polymer chains. Crosslinking prevents polymer dissolution, but may allow a polymer system to imbibe fluid and swell to many times its original size.

Transdermal Delivery Devices

One aspect of the present invention is directed to a transdermal drug delivery system for delivering one or more active agents and/or beneficial substances (e.g drugs) to a biological interface. Such a system can comprise a base element and plurality of microprotrusions formed thereon. In particular embodiments said base element can have a first side and a second side; and said plurality of microprotrusions comprise a plurality of elements which project from the second side of said base element at an angle. In one embodiment with respect to said base element said angle is in the range 45° to 90°, for example in the range 70° to 90°. In a particular embodiment, said angle is about 90°. In particular embodiments of the device, said base element and plurality of microprotrusions can be formed of polymeric materials known to form hydrogels upon absorption of moisture. Suitably, in preferred embodiments, in use, upon insertion into skin the polymeric materials of said microprotrusions and base element can absorb moisture and increase in size to form swollen hydrogels; wherein therapeutic active agents can diffuse through said swollen base element and swollen hydrogel microprotrusions. In particular embodiments, a therapeutic active agent can be provided from a reservoir; wherein said reservoir can be attached to the first side of the base element. In particular embodiments of the device, the reservoir can be a drug dispersed in a suitable matrix material, for example a suitable adhesive or non-adhesive polymer matrix, or a fluid-containing reservoir or contain solid therapeutic active agent(s) for reconstitution by a liquid injected into said reservoir.

In an alternative embodiment of a transdermal delivery device of the invention, an attached reservoir is not present. In such embodiments, one or more therapeutic drug substances or other beneficial substances may be contained within the swellable polymer composition of said base element and plurality of microprotrusions. Said substances can be either dissolved in the swellable polymer composition or suspended in particulate form. Upon insertion into skin and swelling of the microprotrusions, the therapeutic active agents can be released into the skin at a rate determined by the degree of crosslinking of the microprotrusions and the water solubilities of the therapeutic active agents themselves.

A backing layer with an adhesive border extending beyond the area of the base element of the microprotrusions may be used to keep microprotrusion-based devices in place on the skin surface for protracted periods of time, for example up to or greater than 72 hours. The surface of a base element of and, optionally, the microprotrusions themselves, may be coated with an adhesive material, so as to promote retention at the site of application.

In particular embodiments, the active agent(s) can be chemically bonded to the polymer(s) making up the microprotrusions and base elements. In this case, the drug can be released upon insertion into the skin by; dissolution of the microprotrusions, hydrolysis, enzymatic or spontaneous non-catalysed breakage of the bonds holding it to the polymer(s). The rate of drug release can thus be determined by the rate of reaction/bond breakage.

In an alternative embodiment, the polymeric composition of the microprotrusions and/or base elements can be adjusted such that it can be stimulus-responsive. For example, local changes in pH or temperature can alter the properties (eg ability to swell upon imbibing moisture) of the microprotrusions and base elements, such that a change in the rate of delivery of therapeutic active agent(s) occurs. Alternatively, an external stimulus, such as light illumination, can be used to affect a change in the properties of the microprotrusions and base elements, such that a change in the rate of delivery of therapeutic active agent(s) occurs.

In embodiments of arrays of the invention, the polymeric composition of the microprotrusions and base elements can be adjusted such that the surface properties of the device are altered, becoming more hydrophilic, lipophilic, anionic or cationic in character.

Active Agents

The microprotrusion arrays and transdermal delivery devices of the invention may be used to deliver any suitable active agent. For example, the active agent may be a drug, a nutrient or a cosmetic agent. The term drug includes 'beneficial substances' for the treatment or prophylaxis of disease, for example, drug substances, substances that may improve the general health of the skin, for example, vitamins and minerals, and substances that may improve the aesthetic appearance of the skin, for example, by reducing the appearance of wrinkles or improving the degree of hydration of the skin.

Non-limiting examples of drugs suitable for delivery using such a device include oligonucleotides, proteins, enzymes, antigens, nucleic acids, growth factors, polysaccharides as well as smaller molecules, synthetic organic and inorganic compounds such as antibiotics, anti-infectives, hormones, drugs relating to cardiac action and blood flow, drugs for pain control, steroids and sedatives. The administered drug can be for local treatment or regional or systemic therapy. Therapeutically-active doses of medicament can be provided by the microprotrusion arrays.

Optionally the drugs may be water soluble. Indeed, the vast majority of drug substances, having been developed for oral delivery, possess some degree of water solubility, while diagnostic substances dissolved in interstitial fluid are also water soluble. Drug molecules can diffuse through the matrix of the microprotrusions swollen by moisture from the viable skin layers, wherein the degree of swelling controls the rate of drug diffusion.

In embodiments of the transdermal delivery device, the transdermal delivery device can comprise a reservoir or matrix upon which microprotrusions can be attached. In particular embodiments, in use, the reservoir or matrix can comprise an agent to be delivered, for example a drug which, on insertion of the microprotrusion into the skin, flows from the reservoir or matrix through the microprotrusion to the delivery site.

In particular embodiments, agent delivery can occur via simple passive diffusion or can be electrically assisted or pressure assisted.

In embodiments utilising assisted delivery, assisted delivery can be through pressure-driven means, for example, but not limited to a syringe or a pump; wherein in specific embodiments, the syringe or pump can be electrically-driven.

Passive or assisted transdermal delivery of an agent, for example a drug, mediated by microprotrusions of the invention can occur from systems consisting of the microprotrusion arrays coupled with agent-containing reservoirs.

In particular embodiments, prior to flowing through the microprotrusions, an agent to be delivered can be stored in a reservoir or matrix. The reservoirs can be deformable. In particular embodiments, the reservoirs can be sub-divided into a number of chambers wherein each chamber supplies different agents simultaneously or sequentially into the delivery site. Alternatively or additionally, the microprotrusions themselves can be coated with the agent to be delivered. Suitably in such embodiments, the agent can dissolve and diffuse away from the microprotrusion following insertion into skin.

In particular embodiments, a device of the invention and optionally a reservoir or matrix can be incorporated into a wrist band or conveniently worn by a patient.

The rate of drug delivery could be controlled by altering one or several design variables of an array. For example, the number of microprotusions can be varied, as could their diameter and/or height. Application of force may be used to drive drug flow, or some microprotrusions could be filled with a diffusion-limiting material.

Further, to modulate the rate of delivery of a drug through the skin, an agent deliverable by a microprotrusion array of the invention, for example a drug, can be encapsulated within polymeric nanoparticles to further modulate their release from swollen microprotrusions.

Iontophoretic Devices

One aspect of the present disclosure is directed to an iontophoretic transdermal drug delivery system for delivering one or more therapeutic active agents to a biological interface. Such a system can comprise a transdermal delivery device according to the second aspect of the invention. In specific embodiments the therapeutic active agents can be provided from a reservoir. Said reservoir can be a matrix-type (drug-in-adhesive) reservoir or a fluid-containing reservoir or contain solid therapeutic active agent(s) for reconstitution by a liquid injected into said reservoir. In such embodiments the device may further comprise a first electrode and a second electrode at a location different to said first electrode, both electrodes being proximal to said reservoir, a power source, electronic controller and central processing circuit. Application of a potential difference between the electrodes facilitates delivery of therapeutic active agent(s) from said reservoir into the skin by iontophoresis or electroosmotic flow through said swollen base element and microprotrusions.

It will be apparent to those skilled in the art that this aspect of the invention may be combined with one or more of the foregoing aspects, if required.

Sampling Methods

As described herein, the microprotrusions of the invention may be used in the monitoring of levels of substances of diagnostic interest in the body and for the sampling of substances from the skin. Thus in one aspect of the invention, there is provided a device for extraction of skin interstitial fluid or components thereof, said device comprising a microprotrusion array of the invention and a collection chamber. In use, upon insertion into skin, the microprotrusions absorb moisture and increase in size to form swollen microprotrusions; wherein skin interstitial fluid or components thereof can be extracted through said swollen base element and swollen hydrogel microprotrusions into the collection chamber.

Furthermore, the device of the invention may be used for sampling of fluids other then interstitial fluid. For example by applying the device to mucous membranes, for example in the oral cavity, direct blood sampling may be possible.

In suitable embodiments of such a device, the device can comprise detection means. Suitably, in preferred embodiments, the detection means to detect components in the skin interstitial fluid can be electrical or optical.

In particular embodiments, devices used for minimally-invasive monitoring can communicate with and/or comprise a sensor for detection of the analyte of interest and a processor for interpreting the signal generated.

Extraction of skin interstitial fluid can occur via simple passive diffusion, can be electrically-assisted or mechanically assisted. In embodiments wherein extraction is electrically assisted, an electrical current may be applied to the skin. In embodiments of the device, the device can comprise a diaphragm pump wherein, in use, instead of an electrical current extracting fluid from skin, the user-activated diaphragm pump can be attached to an array of microprotrusions.

In another aspect of the invention, the present invention encompasses a reverse iontophoretic device for extraction of skin interstitial fluid or components thereof and subsequent determination of concentration of an analyte of interest. In such an embodiment, the device for extraction of skin interstitial fluid or components thereof can further comprise a first electrode and a second electrode at a location different to said first electrode, both electrodes being proximal to said collection chamber, a power source, electronic controller, central processing circuit and a visual indicator. Application of a potential difference between the electrodes facilitates extraction of skin interstitial fluid or components thereof by iontophoresis or electroosmotic flow through said swollen base element and microprotrusions.

In specific embodiments the device can comprise a third electrode, also being proximal to said collection chamber and in a different location to said first two electrodes. Suitably, this third electrode can act as a bioelectrochemical sensor.

In further alternative embodiments, detection and quantification of an analyte could be by means of chemical reaction, by binding to a substrate or reaction mediated by an enzyme.

For example, the collection chamber can contain a hydrogel loaded with glucose oxidase for detection and quantification of glucose.

The display unit can provide, in the form of a coloured indicator or digital read out, information about the measured level of an analyte of interest. The analyte of interest can be an endogenous chemical, for example but not limited to, glucose or therapeutic active agent(s).

In further alternative embodiments of the iontophoretic device, the first two electrodes may not comprise part of the device, all other elements remaining the same. Instead, following puncture of the stratum corneum, skin interstitial fluid or components thereof can diffuse passively through said swollen base element and swollen hydrogel microprotrusions into the collection chamber.

Alternatively, the microprotrusions themselves may comprise the sensing element. They may be made electrically conducting by incorporation of a suitable electrolyte and thus detect chemical changes in the composition of skin extracellular fluid electrochemically. Alternatively, the matrix of the base element and microprotrusions can be loaded with e.g. glucose oxidase for detection and quantification of glucose. In an application for sensing based on a chemical reaction, binding to a substrate or reaction mediated by an enzyme, the relevant chemical reactant, substrate or enzyme could be immobilised within the matrix of the base element and microprotrusions. Wave guides can also be incorporated into the microprotrusion array to direct light into skin for detection using means such as a pH-sensitive dye for colour evaluation, for example. Similarly, light could be transmitted through the microprotrusions for measurement of blood glucose based on infrared spectra.

In another aspect of the invention, the present disclosure is directed to a closed-loop iontophoretic transdermal drug delivery system for delivering one or more therapeutic active agents to a biological interface and subsequent determination of the concentration of the delivered agent in skin interstitial fluid. Such a system comprises a base element and a plurality of microprotrusions formed thereon. In particular embodiments said base element has a first side and a second side and said plurality of microprotrusions comprise a plurality of elements which project from the second side of said base element along a longitudinal axis that is at an angle with respect to said base element. Suitably, in particular embodiments, said base element and plurality of microprotrusions are fabricated from polymeric materials known to form hydrogels upon absorption of moisture. Suitably, in embodiments of the system, the system can further comprise a reservoir wherein the reservoir can be attached to the first side of the base element; and wherein said reservoir can be a matrix-type (drug-in-adhesive) reservoir or a fluid-containing reservoir or contain solid therapeutic active agent(s) for reconstitution by a liquid injected into said reservoir. In use, upon insertion into skin, said microprotrusions and base element absorb moisture and increase in size to form swollen hydrogels; wherein therapeutic active agents can be delivered through said swollen base element and swollen hydrogel microprotrusions from a reservoir;

The system can further comprise a first electrode and a second electrode at a location different to said first electrode, both electrodes being proximal to said reservoir, a power source, electronic controller central processing circuit and a visual indicator. Application of a potential difference between the electrodes facilitates delivery of therapeutic active agent(s) from said reservoir into the skin by iontophoresis or electroosmotic flow through said swollen base element and microprotrusions. The system can further comprise a collection chamber attached to the first side of the base element, or a separate base element and a third electrode and a fourth electrode at a location different to said third electrode, both electrodes being proximal to said collection chamber, the third and fourth electrodes and collection chamber being located at a different region of the base element to the first and second electrodes and the reservoir, or attached to a separate base element. In use, application of a potential difference between the third and fourth electrodes facilitates extraction of skin interstitial fluid or components thereof by iontophoresis or electroosmotic flow through said swollen base element and microprotrusions. A fifth electrode, also being proximal to said collection chamber and in a different location to said first four electrodes, can be provided to act as a bioelectrochemical sensor. Alternatively, detection and quantification could be by means of another chemical reaction, by binding to a substrate or reaction mediated by an enzyme. A display unit can provide, in the form of a coloured indicator of digital read out, information about the measured level of therapeutic active agent(s) of interest.

In particular embodiments a delivery part of the device can deliver therapeutic active agent(s) according to the levels of the agent(s) measured by the sensing part of the device, so as to tailor delivery to an individual patient. Alternatively, therapeutic active agent(s) may be delivered at a pre-defined or user-defined rate and the levels of the agent simply monitored.

In particular embodiments, sampling of skin interstitial fluid can be performed by reverse iontophoresis through the swollen microprotrusions. In particular embodiments an iontrophoretic device can comprise electrodes capable of detecting an electrical signal. In such embodiments, an electronic controller can facilitate body-fluid sampling from skin through the microprotrusion by reverse iontophoresis and an electrode can detect an electrical signal in the manner of a bioelectrochemical sensor.

Alternatively, in embodiments of an iontophoretic device the microprotrosions can comprise a gel that has a sensing functionality.

In an embodiment of a device for sensing based on binding to a substrate or reaction mediated by an enzyme, the substrate or enzyme can be immobilised in or on the microprotrusion. In these embodiments or others, wave guides can also be incorporated into the microprotrusions or iontophoretic device to direct light to a specific location, or for detection, for example, using means such as a pH-sensitive dye for colour evaluation. Similarly, light can be transmitted through the microprotrusions for measurement of blood glucose based on infrared spectra. Alternatively, a colour change can be measured in the presence of immobilised glucose oxidase.

Such an iontophoretic device can be incorporated into a wrist band and conveniently worn by a patient for drug delivery, sampling of biological fluid or both.

Analytes

Essentially any drug, bioactive agent or endogenous biochemical could be sampled using the present invention. The only restriction is that the analyte of interest must be present in skin interstitial fluid at levels that can be accurately correlated with plasma concentrations of that analyte. Examples include, but are not limited to, glucose, sodium, potassium, alcohol, lactate (important for athletes), drugs of abuse (e.g. cannabinoids, amphetamines, cocaine, and opioids), and nicotine metabolites (e.g. cotinine) as well as therapeutic drug substances that a patient may be taking for one or more medical conditions. The invention would be particularly useful for drugs with narrow therapeutic windows.

As with applications for the purpose of drug delivery, the properties of the microprotrusion-based device can be suitably altered to achieve the desired properties for sensing purposes. It is possible to incorporate both delivery and sensing functions into a single device, forming a closed-loop drug delivery system. In this way, patient monitoring and responsive drug delivery can be achieved from a single integrated system, thus achieving unprecedented disease control & radical improvements in health-related-quality-of-life.

Further Applications

The potential applications of microstructured devices are not limited to transdermal drug delivery and interstitial fluid sampling.

One of the greatest number of prospective applications of commercial interest is thought to be in the cosmetic industry, specifically in dermatological and beauty products. Use of the microprotrusion array of the invention to deliver cosmetic compounds or nutrients or various skin structure modifiers, would be advantageous as a subject receiving said agents would not have to visit a cosmetic surgery clinic.

In particular embodiments, the microprotrusions of the invention can be used to apply semi-permanent or permanent markings to skin, or to apply semi-permanent subcutaneous makeup or other cosmetic compounds to skin. This may be particularly advantageous, as by using the microprotrusion array of the present invention, the application of tattoo-like graphics or other identifications, subcutaneous makeup, conditioning agents and agents likely to affect the appearance of the skin, including, for example, but not limited to, gamma amino butyric acid (GABA) and botulinum toxin ("Botox") would typically not penetrate the dermal layer of the skin. The application procedure would therefore be relatively painless.

The applications of the technology described herein are not by any means limited to those described in detail. In fact, other uses of this technology will be obvious to those skilled in the art. These applications include, but are not limited to, use as a scaffold for tissue engineering, formation of biofilm models and transdermal delivery of active agents via stents. The invention will now be described further in the following non-limiting examples with reference made to the accompanying drawings in which:

FIG. 1 is an elevational view in partial cross-section of a silicon master used to micro mould protrusions (1 Micro protrusion manufactured in silicon shown in cross-section; 2 adjacent micro protrusion manufactured in silicon shown in cross-section, 3 silicon base plate, L1 height of micro protrusion above upper face of base plate 4, D1—apical distance between micro protrusions 1 and 2)

FIG. 2 is an elevational view in partial cross-section of an overlaid casting material intended to replicate the outline geometry of a silicon master in FIG. 1 in a second step of the moulding procedure (4 overlaid silicone elastomeric material, 3 micro protrusion array manufactured in silicon)

FIG. 3 is an elevational view in partial cross-section of the elastomeric material 4 removed from 3 in FIG. 2 showing cross-sectional relief 5 of micro protrusions 1 and 2 in a third step of the moulding procedure (5 relief of micro protrusion, 4 elastomeric mould);

Figure 1:
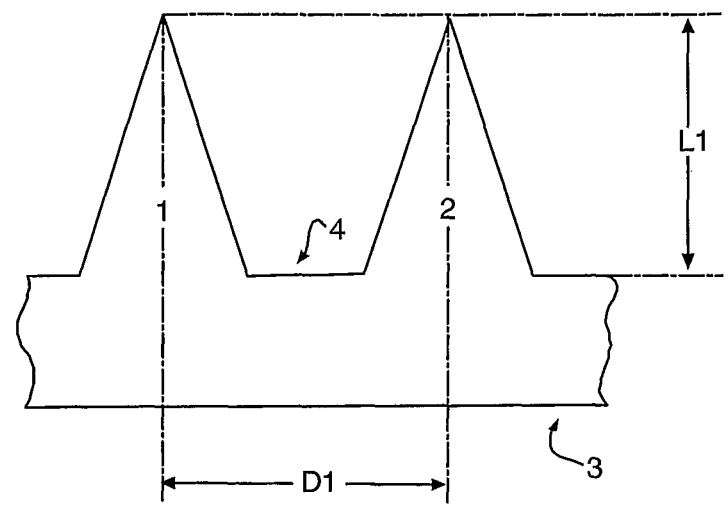
Figure 2:
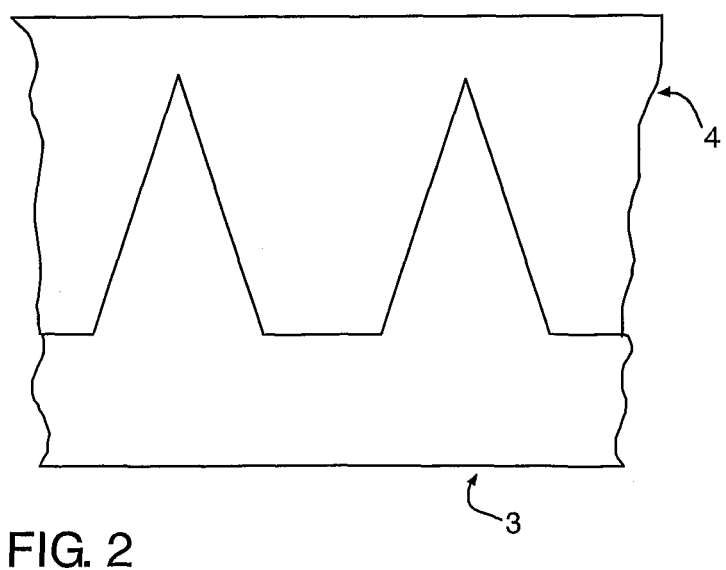
Figure 3:
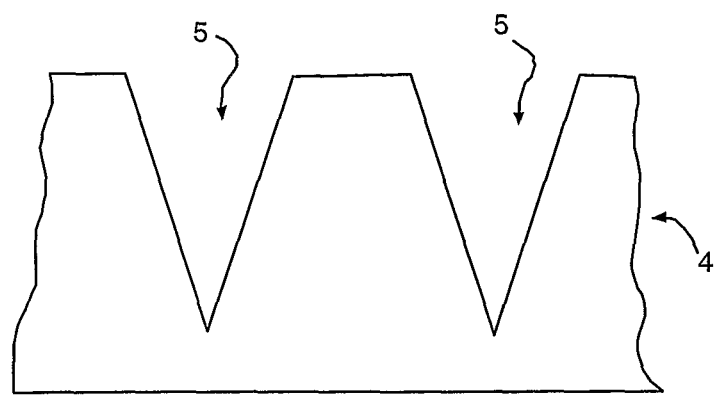
Figure 4:
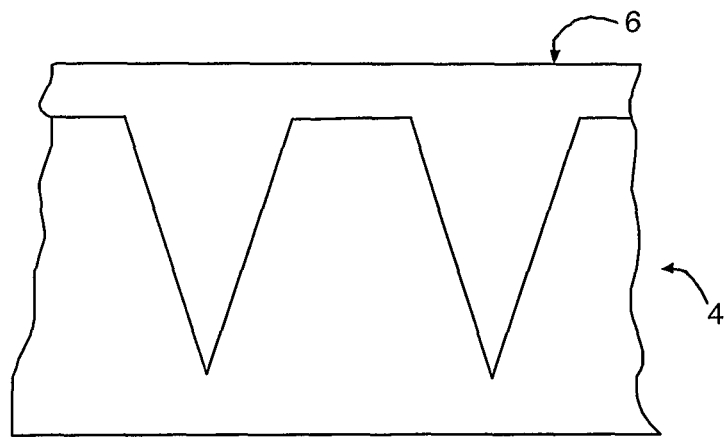
FIG. 4 is an elevational view in partial cross-section of a cast polymeric solution 6 introduced into the mould 4 prepared in FIG. 3 in a fourth step of the moulding procedure (6 cast polymer solution, 4 elastomeric mould prepared as shown in FIG. 3)
Figure 5:
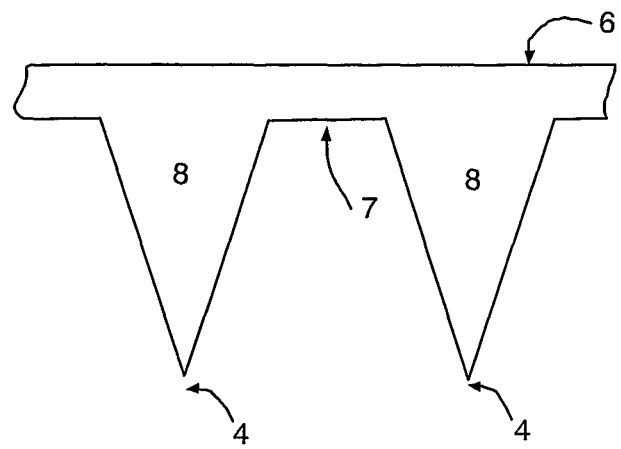
FIG. 5 is an elevational view in partial cross-section of a cross-linked array of micro protrusions as removed from the mould in FIG. 4 in a fifth step of the moulding procedure (4—apex of polymeric micro protrusion, 8—body of polymeric micro protrusion, 7—spacing between micro protrusions as measured along the supporting base plate, 8—top surface of supporting polymeric base plate)
Figure 6:
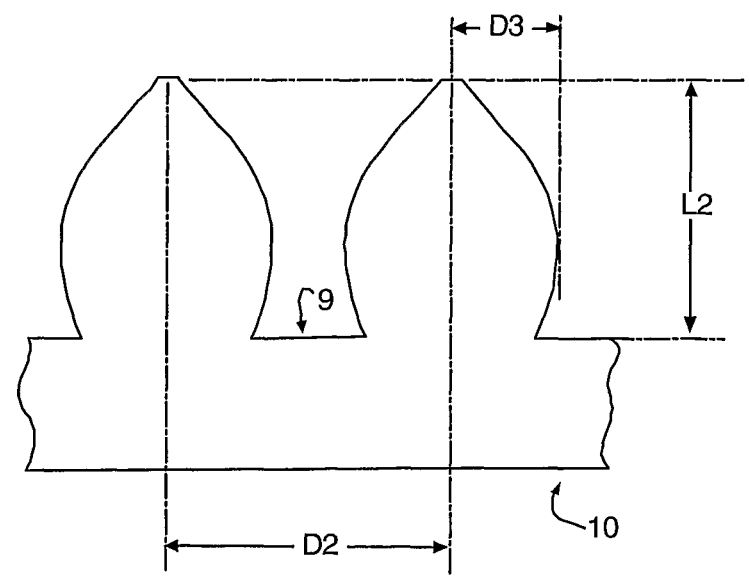
Figure 7:
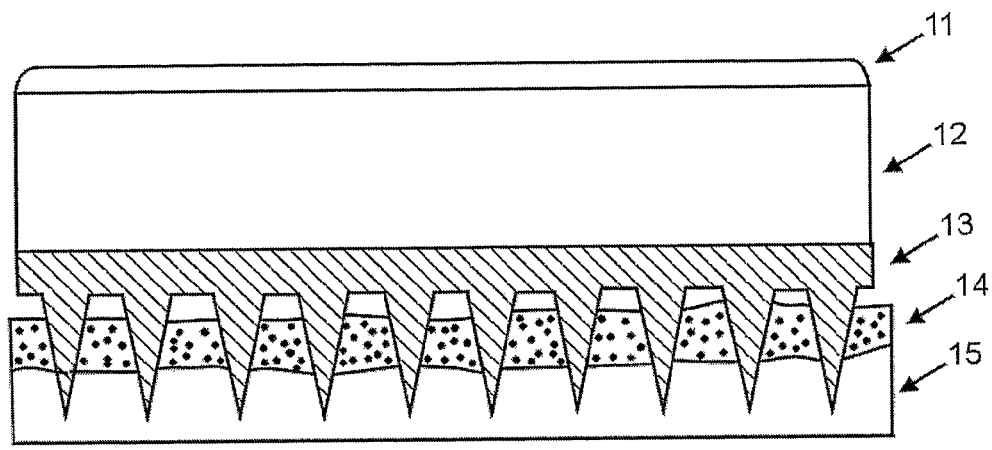
Figure 8:
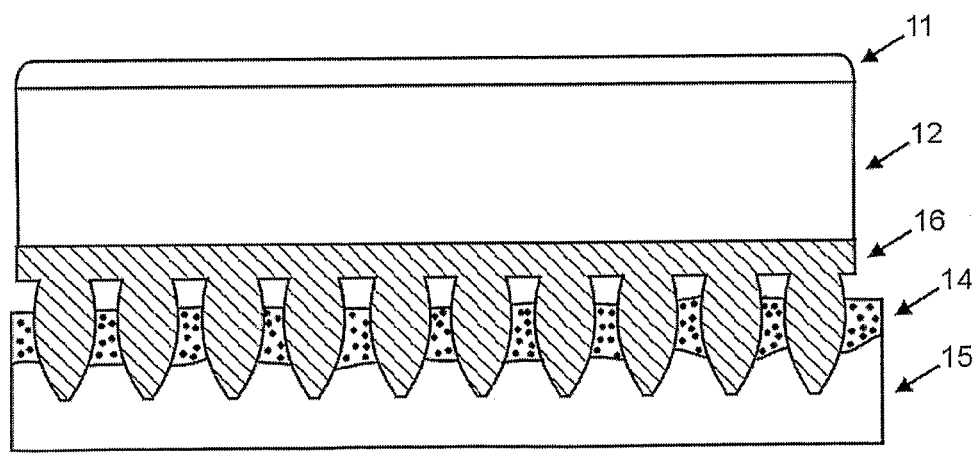
Figure 9:
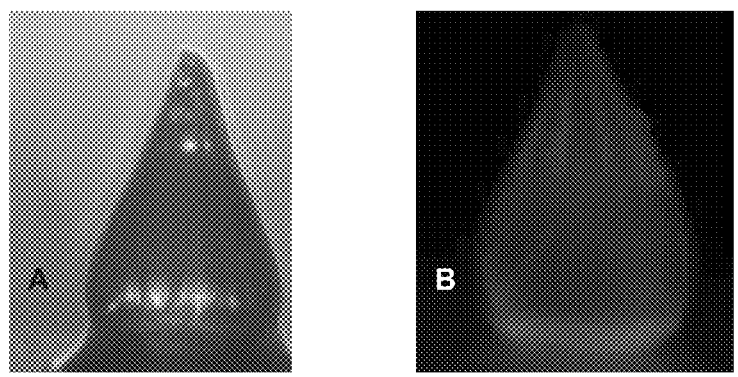
Figure 10:
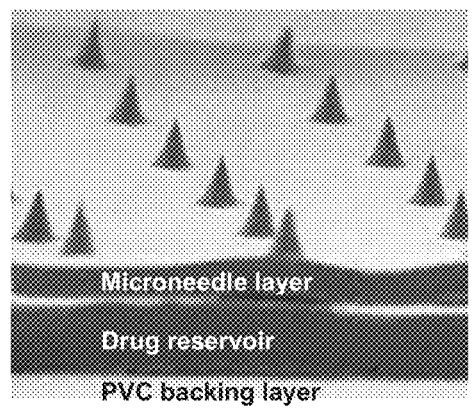
Figure 11:
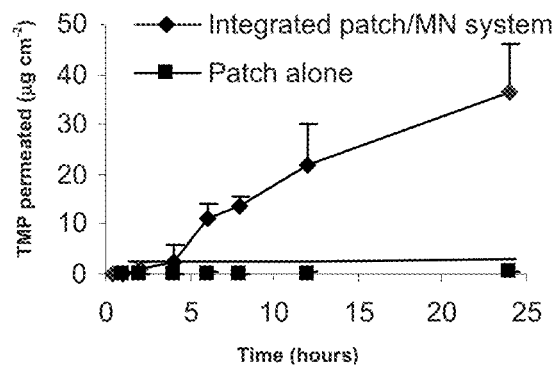
Figure 12:
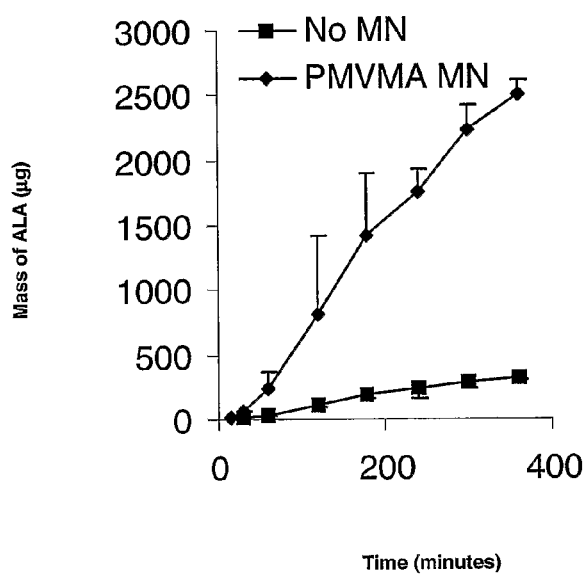
Figure 13:
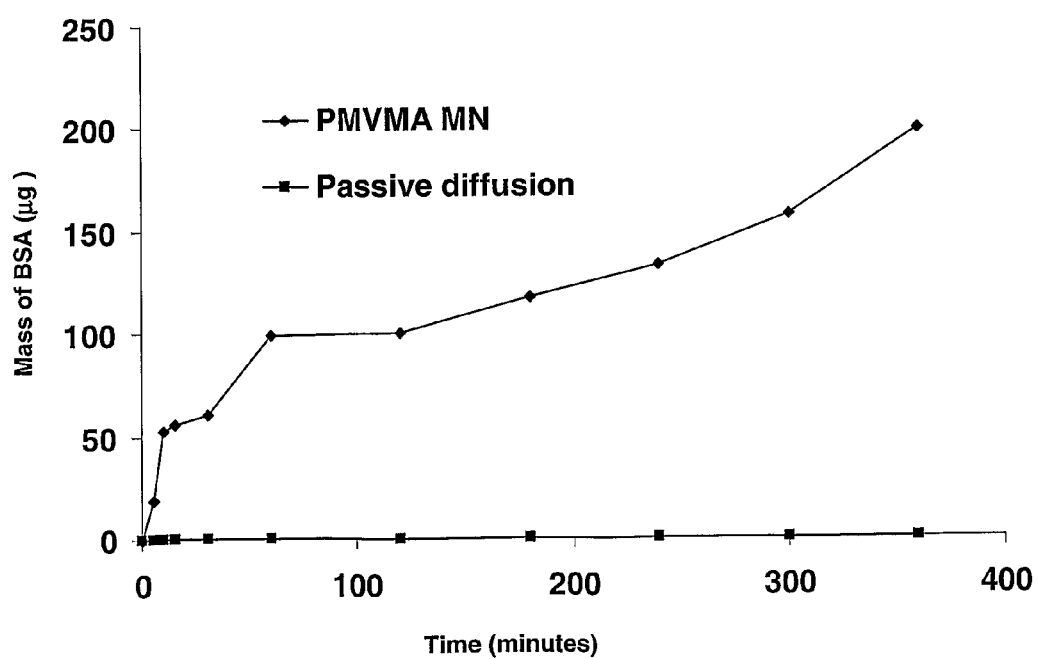
Figures 14, 15:
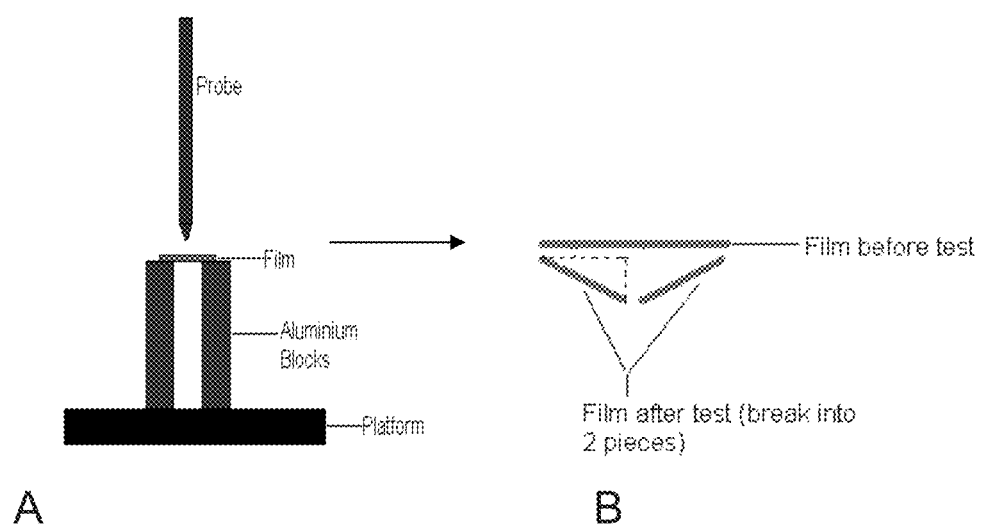
Figure 20:
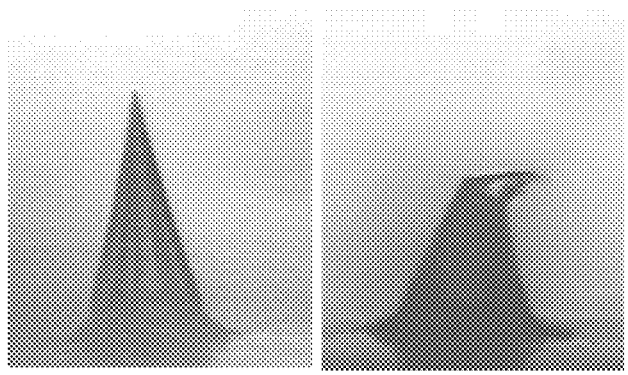
Figure 20:
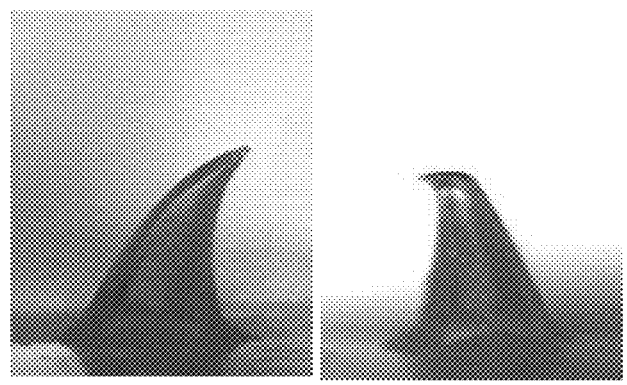
Figure 20:
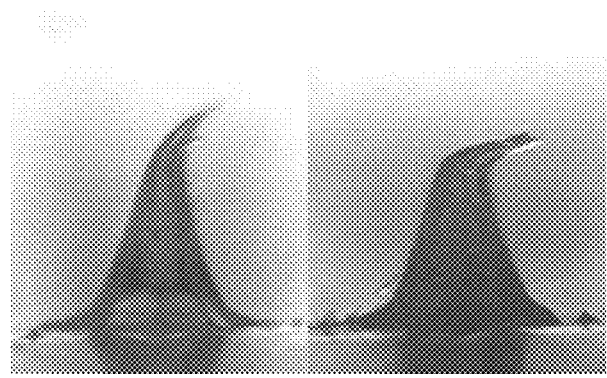
Figure 21:
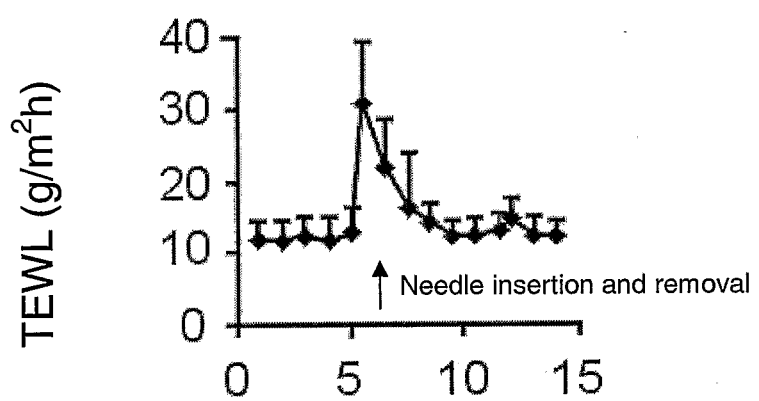
Figure 22:
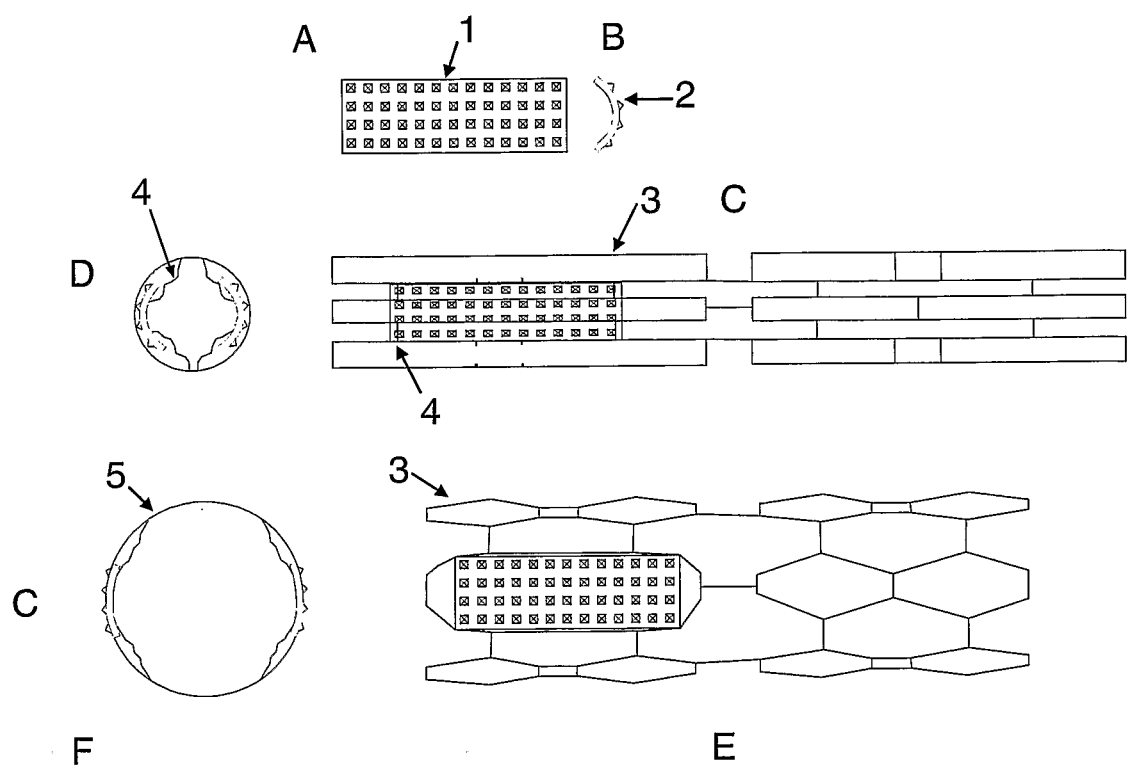
Figure 23:
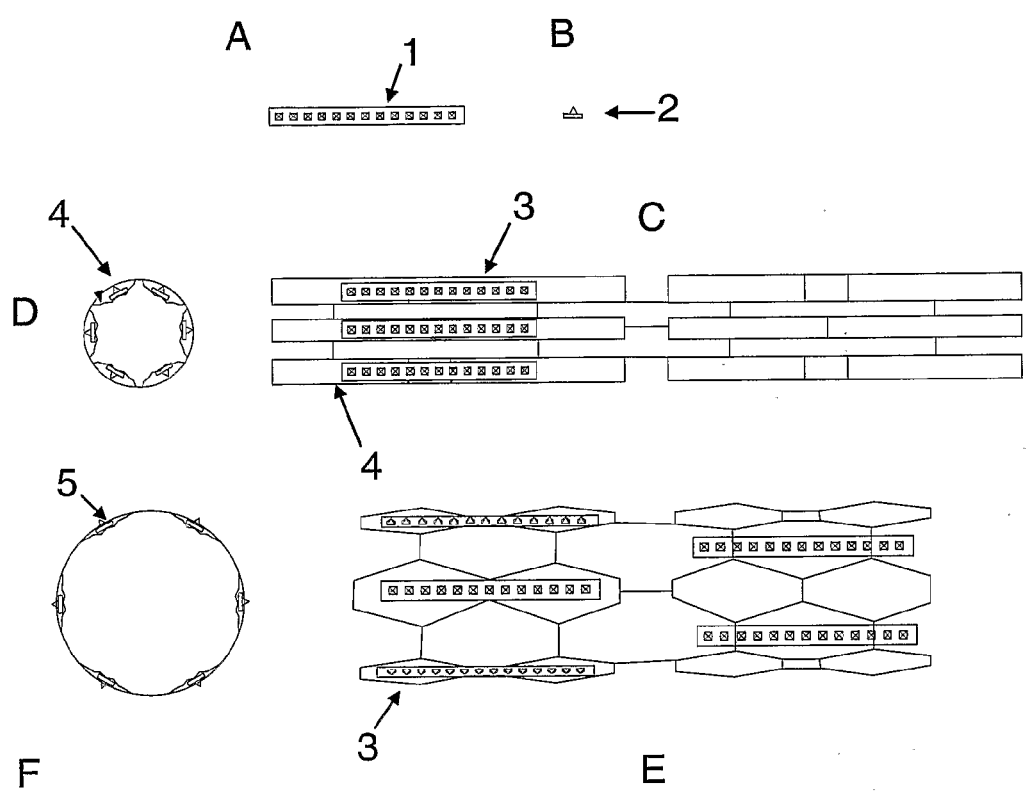

FIG. 6 is an elevational view in partial cross-section of a cross-linked array of micro protrusions that have undergone an hydration-induced alteration in geometric shape and alteration in drug diffusivity (10—hydration swollen supporting base plate, 9—spacing between hydration swollen micro protrusions along swollen base plate, L2—height of, D3—half maximum thickness of hydration swollen micro protrusion, D2—apical distance between hydration swollen micro protrusions);

FIG. 7 is an elevational view in partial cross-section of a cross-linked array of micro protrusions as constructed using the principles of the present invention and forming part of a transdermal delivery system for the delivery of a beneficial substance (11—protective backing layer, 12—reservoir containing beneficial substance as either a solution or suspension in a pharmaceutical vehicle, 13—cross-linked array of micro protrusions, 14—stratum corneum of skin, 15—viable epidermis);

FIG. 8 is an elevational view in partial cross-section of a cross-linked array of micro protrusions as constructed using the principles of the present invention and shown in FIG. 7 that have undergone a hydration-induced alteration of physical attributes (11—protective backing layer, 12—reservoir containing beneficial substance as either a solution or suspension in a pharmaceutical vehicle, 16—cross-linked array of micro protrusions that have undergone an hydration-induced alteration in geometric shape and alteration in substance diffusivity, 14—stratum corneum of skin, 15—viable epidermis);

FIG. 9 shows a swollen poly(methyl/vinyl ether/maleic acid-co-glyceride) microneedle after removal from porcine skin (A) and also shows diffusion of the fluorescent compound meso-Tetra (N-methyl-4-pyridyl) porphine tetra tosylate (MW 1363.6 Da) through the matrix of the swollen microneedle;

FIG. 10 shows an integrated transdermal patch system composed of a poly(methyl/vinyl ether/maleic acid-co-glyceride) microneedle layer, a matrix-type drug reservoir composed of water, poly(methyl/vinyl ether/maleic acid) and tripropyleneglycol monomethylether and an impermeable backing layer composed of medical grade poly(vinylchloride);

FIG. 11 shows delivery of meso-Tetra (N-methyl-4-pyridyl) porphine tetra tosylate (TMP) across full thickness murine skin from an aqueous-based matrix-type drug reservoir containing 19.0 mg TMP $cm^{-2}$ with and without integrated poly(methylvinylether/maleic acid-co-glyceride) (PMVMA) microneedle (MN) array;

FIG. 12 shows cumulative transport of 5-aminolevulinc acid (ALA, MW 167 Da) across full thickness murine skin from an aqueous-based matrix-type drug reservoir containing 38,000 µg ALA $cm^{-2}$ with and without integrated poly (methylvinylether/maleic acid-co-glyceride) (PMVMA) microneedle (MN) array;

FIG. 13 shows cumulative transport of bovine serum albumin (BSA, MW 66,000 Da) across a Silescol® membrane, used universally as a stratum corneum model, following puncture with poly(methylvinylether/maleic acid-co-glyceride) (PMVMA) microneedles (MN) attached to aqueous fluid drug reservoirs containing 10,000 µg BSA $cm^{-3}$;

FIG. 14 shows the polymer concentrations of films made from PMVE/MA and PEG and other commonly-used hydrophilic polymers i.e. Amylopectin, CMC, Poly (HEMA), PVA and HEC;

FIG. 15A shows a schematic diagram of the TA-XT2 Texture Analyzer;

FIG. 15B is a schematic diagram showing a polymeric film before and after break, distance traveled after break and angle of deflection at the film's breaking point using the TA-XT2 Texture Analyzer;

FIG. 16 shows the percentage swelling of Amylopectin, CMC, Poly (HEMA), PVA and HEC;

FIG. 17 shows the percentage swelling of PMVE/MA and PEG (2:1) crosslinked films;

FIG. 18 shows the buckling strength of Amylopectin, CMC, Poly (HEMA), PVA, HEC and PMVE/MA and PEG crosslinked films;

FIG. 19 shows the mechanical strength of polymeric microprojection arrays made from PMVE/MA and PEG crosslinked films, Amylopectin, CMC, Poly (HEMA), PVA and HEC;

FIG. 20 shows polymeric microneedle arrays upon preparation (left hand images) and after mechanical testing with the TA-XT2 Texture Analyser (right hand images);

FIG. 21 shows the measurement of transepidermal water loss (TEWL) using silicone microneedle arrays on *Strateum corneum* of human volunteers (n=5);

FIG. 22 (A-F) shows elevational and cross sectional views of a flexible slab-type microneedle array (A,B) and a stent in a collapsed position (C,D) and in an expanded position (E,F); and FIG. 23(A-F) shows elevational and cross sectional views of a rigid single file type microneedle array (A,B) and a stent in a collapsed position (C,D) and in an expanded position (E,F).

EXAMPLES

Example 1

Preparation of Microprotrusion Arrays from Polymers known to form Hydrogels

The preparation of microprotrusion arrays composed of swellable polymers is shown schematically in FIGS. 1 to 6. FIG. 7 illustrates a cross-linked array of micro protrusions as constructed using the principles of the present invention and forming part of a transdermal delivery system for the delivery of a beneficial substance FIG. 8 illustrates the effect of hydration on the cross-linked array of micro protrusions as constructed using the principles of the present invention and shown in FIG. 7, showing a hydration-induced alteration of physical attributes.

Elemental silicon microneedle arrays were prepared using a wet etch process using potassium hydroxide etching. Such arrays were then covered in liquid poly(dimethylsiloxane) elastomer in a suitable circular mould. The elastomer was then cured (60° C., 2 hours) and the silicon array removed to yield a micromould. This micromould was then filled with an aqueous gel containing 20% w/w poly(methyl vinyl ether/maleic acid) and 10% w/w glycerol. The micromould was placed in a circular outer mould and a lid attached. The entire assembly was centrifuged (3600 g, 15 minutes) to ensure complete filling. The lid was removed and the water allowed to evaporate. The replicate polymeric array was then crosslinked by heating to 60° C. for 4 hours to initiate an esterification reaction (McCarron et al (2004), *J Appl Polym Sci*, 91, 1576-1589). Thus, crosslinked poly(methyl vinyl ether/maleic acid-co-glyceride) microneedles were produced.

Example 2

Study on Swelling of Microprotrusion Arrays in Skin and Diffusion of Drug Substances Through the Matrix of Swollen Microprotrusions Poly(methyl vinyl ether/maleic acid-co-glyceride) microneedles were inserted into neonate porcine skin with the aid of gentle pressure and removed after four hours before visualisation using a light microscope (FIG. 9A). In a similar experiment, poly(methyl vinyl ether/maleic acid-co-glyceride) microneedles with an attached aqueous-based matrix-type drug reservoir (FIG. 10) containing 19.0 mg cm$^{-2}$ of the fluorescent photosensitiser drug meso-Tetra (N-methyl-4-pyridyl) porphine tetra tosylate (MW 1363.6 Da), were inserted into neonate porcine skin with the aid of gentle pressure and removed after four hours before visualisation using a light microscope (FIG. 9B). This demonstrates conclusively that drugs contained in a reservoir attached to the microprotrusion base element can diffuse through the swollen hydrogel. The diffusing meso-Tetra (N-methyl-4-pyridyl) porphine tetra tosylate imparts a characteristic red fluorescence to the entire microneedle.

Example 3

Delivery of a Large Water Soluble Drug Across Full Thickness Skin

The physicochemical characteristics (MW >600 Da, very water soluble) of the photosensitiser drug meso-Tetra (N-methyl-4-pyridyl) porphine tetra tosylate (TMP) (MW 1363.6 Da) make it unsuitable for efficient transport across the stratum corneum barrier of skin. In this study, a matrix-type drug reservoir containing 19.0 mg TMP cm$^{-2}$ was prepared and attached to a poly(methylvinylether/maleic acid-co-glyceride) (PMVMA) microneedle array. This system was pressed into full thickness murine skin, mounted as the barrier membrane in a Franz diffusion cell, with the aid of gentle pressure. TMP appearing in the receiver compartment was determined by fluorescence spectroscopy over a period of 25 hours. The results are shown in FIG. 11 and indicate that sustained delivery of TMP across full thickness skin is possible. Importantly, this illustrates that hydrogel microneedles keep puncture holes in the stratum corneum open for prolonged periods of time and that compression or blockage of swollen hydrogel microneedles does not occur.

Example 4

Delivery of a Small Very Water Soluble Drug Across Full Thickness Skin

An identical experiment to that described in Example 3 was performed again. The only difference was that the small very water soluble photosensitiser precursor 5-aminolevulinc acid (ALA, MW 167 Da) was used instead of TMP. ALA is well known to exhibit poor permeation across normal stratum corneum. Rapid, and greatly enhanced ALA delivery across full thickness murine skin from an aqueous-based matrix-type drug reservoir containing 38,000 μg ALA cm$^{-2}$ was observed using the integrated poly(methylvinylether/maleic acid-co-glyceride) microneedle array (FIG. 12).

Example 5

Delivery of a Large Protein Across a Model Membrane

The large molecular weights and water solubilities of peptide and protein drugs preclude successful transdermal administration. However, in this example, delivery of significant levels of the large protein bovine serum albumin (BSA, MW 66,000 Da) across a Silescol® membrane used Worldwide as a stratum corneum mimic was shown to be possible using poly(methylvinylether/maleic acid-co-glyceride) (PMVMA) microneedles (MN) attached to aqueous fluid drug reservoirs containing 10,000 µg BSA cm$^{-3}$ (FIG. 13).

Example 6

Comparison of Mechanical and Swelling Characteristics of Microneedle Arrays Prepared from PMVE/MA and PEG and Other Commonly-Used Hydrophilic Polymers The following example describes a number of experiments showing that microneedle arrays prepared from aqueous gels of poly(methyl/vinyl ether/maleic acid) (PMVE/MA) or similar, related, polymers (e.g. poly(methyl/vinyl ether/maleic anhydride) optionally crosslinked using polyhydric alcohols (e.g. glycerol, propylene glycol (poly(ethylene glycol)-(PEG) exhibit particularly good mechanical and swelling characteristics to microneedle arrays prepared from other commonly-used hydrophilic polymers.

Methods
1. Preparation of Polymeric Films
(a) Preparation of Crosslinked Films from PMVE/MA and PEG:

Aqueous gels containing PMVE/MA (at 10%, 15% and 20%, w/w) and PEG 10,000 in a polymer:crosslinker ratio of 2:1 were prepared and films were prepared by slowly pouring the gels into a mould consisting of a release liner, siliconised side-up, secured to a Perspex base plate using a stainless steel clamp. The gels were evenly spread over the mould area by placing them on a levelled surface and dried for 48 hrs at room temperature to produce films. They were then crosslinked ("cured") at 80° C. over 24 hrs.

(b) Preparation of Other Polymeric Films:

Five different hydrophilic polymers (amylopectin, carboxymethyl cellulose, poly(vinyl alcohol), hydroxyl ethylcellulose and poly(HEMA) were selected for investigation of swelling properties. Films were prepared as described above using the polymer concentrations in FIG. 14, except for poly(HEMA), which was prepared by heating liquid HEMA monomer, containing 2% w/w of the initiator benzoil peroxide and 5% w/w of the crosslinker ethylene glycol-dimethacrylate, in a suitable three-sided mould at 80° C. for 2 hours.

Swelling Studies

Segments of each type of film (1.0 cm$^2$) had their initial weight i.e. $m_o$ recorded. The film samples were then swollen in 30 ml of 0.1 M Phosphate buffer pH 7.4 at room temperature. At regular intervals, film segments were removed, blotted with filter paper to eliminate excess surface water and their swollen weight i.e. $m_t$ recorded. The percentage swelling was then determined using Equation 1:

$$\% \text{ Swelling} = \left(\frac{m_t - m_o}{m_o}\right) \times 100\% \quad \text{(Equation 1)}$$

Buckling Test of Films

The force required to break each film formulation was tested using a TA-XT2 Texture Analyzer (Stable Microsystems, Haslemere, UK), previously calibrated with 2.0 Kg load weight (FIG. 15A). Film segment (1.0 cm×1.5 cm) was fixed on the stage and the probe was moved at a speed of 2.0 mm/sec until the film was broken in the middle (FIG. 15B).

Preparation and Mechanical Testing of Microneedle Arrays

Microneedle arrays were prepared using the gel formulations outlined above. Such gels were placed in inverse poly(dimethylsiloxane) moulds, made using silicon microprotrusion array master templates, and centrifuged (3600 g, 15 min). Formed polymeric arrays were then dried at ambient conditions for 48 hours. Poly(HEMA) microneedle arrays were prepared using the modified technique as described above for polymeric films. Arrays prepared using PEG 10,000 were then crosslinked at 80° C. for 24 hours.

In order to determine the force necessary for mechanical fracture of polymeric microneedles, the Texture Analyser was again employed. An axial compression load (i.e. force applied parallel to the vertical microneedle axes) was applied to the arrays to deduce the changes that occur in their structures. Microneedle arrays were attached to the moving testing probe using double-sided adhesive tape. The test station pressed the arrays against a flat block of aluminium of dimensions 9.2 cm×5.2 cm at a rate 0.5 mm/s with a known force of 0.05 N for 30 s. Pre-test and post-test speed were 1.0 mm/s and the trigger force was set at 0.049 N. Prior to fracture testing, all microneedles of each array were examined using a digital microscope (GE-5 Digital Microscope, View Solutions Inc, Ontario, Canada) under the magnification 180×. After fracture testing, all microneedles were also visualised in the same way to determine the impact of the force applied and an image that was representative was recorded. The height of the microneedles after testing was measured using the ruler function of the microscope software so that the percentage change in the microneedle height could be calculated. Data were reported as the force per microneedle which was required to deform the microneedle. All microneedles used for mechanical fracture testing were 280 µm tall and had constant tip radii, wall thickness and wall angle.

FIG. 16 shows that minimal swelling was observed in films prepared from amylopectin and CMC, which then dissolved within 6 hours. HEC films did not swell, but dissolved rapidly within 15 min. Poly(HEMA) films swelled relatively slowly, only gaining an additional 46% of additional weight after 6 hours. PVA films had quadrupled in weight after 6 hours. In contrast (FIG. 17), films prepared from PMVE/MA crosslinked with PEG 10,000 exhibited rapid swelling. This was particularly apparent in films prepared from gels containing 10% w/w PMVE/MA, which had approximately doubled in weight after only 15 min. By 6 hours, films prepared from PMVE/MA crosslinked with PEG 10,000 had gained over 10 times their original weights.

Films prepared from amylopectin and CMC exhibited an appreciable degree of shrinkage upon drying, such that the films formed were extremely hard and showed considerable warping. Films prepared from PVA and hydroxymethylcellulose (HEC) were not hard and were quite flexible. Following crosslinking, films prepared from PMVE/MA crosslinked with PEG 10,000 were inflexible, hard and rigid in nature. Amylopectin films were relatively brittle and did not undergo mechanical testing. CMC films required a considerable force (77.0 N) to break, in contrast to poly(HEMA) films (4.0 N), which were still quite strong. The force required to break films prepared from PMVE/MA crosslinked with PEG 10,000, which were not brittle in nature, increased with increasing polymer content in the original gel (FIG. 18).

Microneedle arrays prepared from PMVE/MA crosslinked with PEG (in this case PEG 10,000) formed perfectly, giving good replication of the original silicon structures. No warping or drooping was observed. As can be seen from FIG. 19, such microneedle arrays exhibited considerably greater mechanical strengths than those prepared from other polymers, as evidenced by lower height reductions for a given applied force. Importantly, microneedle arrays prepared from PMVE/MA crosslinked with PEG did not shatter. This is in contrast to those prepared from poly(HEMA), which exhibited the next best mechanical strengths as seen in FIG. 20. FIG. 20 (A-F) shows polymeric microneedle arrays upon preparation (left hand images) and after mechanical testing with the TA-XT2 Texture Analyser (right hand images). The microneedles comprising of Amylopectin were sharp but thin, whilst the base was deformed, uneven, corrugated and brittle (FIG. 20A). Those made from CMC indicate that the microneedle tips were slightly bent towards one side whilst the base was even but concave (FIG. 20B). HEC microprotrusions were thin, slightly bent and the base was very flexible and thin (FIG. 20C). Those microneedles made from pHEMAMNs were properly shaped with a flat base; however, the tip shattered upon force application (FIG. 20D). PVA microneedles were sharp, properly formed whilst the base was corrugated, uneven with numerous air bubbles (FIG. 20E). Those microneedles comprising of PMVE/MA 20%:PEG 10,000 were shaped perfectly with a flat base which was even, uniform and only slight bending upon force application (FIG. 20F). Those microneedles remained intact.

Polymeric microneedle arrays should be hard enough to pierce the stratum corneum, but should not break or bend upon application. Preferably, once inserted, they should swell rapidly, and to a significant extent, without dissolving, to allow sustained drug delivery through their swollen matrices. The present inventors have demonstrated conclusively here that Gantrez®-type polymers such as PMVE/MA, optionally crosslinked, e.g. with PEG 10,000 is a particularly excellent material, in terms of swelling capacity, mechanical strength, formation of microneedle arrays and strength of formed arrays. Although out of the materials tested, PMVE/MA crosslinked with PEG 10,000 has been exemplified as having the most ideal material qualities for use in microneedle arrays as described herein, it is assumed that any of the polymers as claimed for use in the invention, being optionally crosslinked e.g. with a polyhydric alcohol, such as PEG 10,000, would be applicable for use in such microneedle (i.e. microprotrusion) arrays.

Example 7

Assessment of *Strateum corneum* Permeability with Silicon Microneedle Arrays Using Measurement of TEWL Preliminary experiments, using human volunteers (n=5), showed microprojection-created holes in the stratum corneum close within about 5 minutes. Silicon microneedle arrays with 100 microneedles per $cm^2$, were applied for 30 seconds to the upper arm of the volunteers using finger pressure only. Each microneedle was pyramidal in shape; with a base width of approximately 250 µm and a height of approximately 280 µm.

*Stratum corneum* permeability was assessed using measurement of transepidermal water loss (TEWL), a technique used worldwide for such purposes. The results show only a temporary increase in TEWL, which quickly returns to normal (FIG. 21). Thus may create problems for silicone microneedle-based systems that are applied and removed.

Example 8

Stents

FIG. 22(A-C) demonstrates an embodiment of the present invention as described herein showing a stent comprising a flexible slab-type microneedle array. FIG. 22 shows an elevational view (A) and a cross-sectional view (B) of the flexible slab-type microneedle array (1) as described herein. The cross-sectional view (A) shows the convex curvature of the microneedle array. FIG. 22C shows an elevational view of the stent in a collapsed position comprising a metal framed stent (3) and the flexible slab-type microneedle (1) of FIG. 22A integrated within said stent (3) by means of metal guide wires (4). FIG. 22D shows a cross-sectional view of FIG. 22C showing the convex array (2) of FIG. 22A below the outer circumference of the stent (3) wherein the convex array (2) is supported by metal guide wires (4).

FIG. 22E is an elevational view of the stent (3) in a balloon-inflated expanded position whilst FIG. 22F is a cross-sectional view of FIG. 22E showing the flattened array (5) following frame extension of the stent (3). The microneedles now protrude beyond the outer circumference.

FIG. 23(A-F) demonstrates a modification of the stent of the present invention as described herein showing a stent comprising rigid single file-type microneedle array strips. FIG. 23 shows an elevational view (A) and a cross-sectional view (B) of a rigid single file-type microneedle array strip. FIG. 23C shows an elevational view of the stent in a collapsed position comprising a metal framed stent (3) and three rigid single file-type microneedle array strips (1) of FIG. 23A integrated within said metal framed stent (3) by means of metal guide wires (4). FIG. 23D demonstrates a cross-sectional view of FIG. 23C showing the microneedle strips (1) below the circumference of the stent (3) wherein the microneedle strips (1) are supported by metal guide wires (4).

FIGS. 23E and 23F show elevational and cross-sectional views respectively of the stent (3) in a balloon-inflated expanded position. FIG. 23F shows the elevated strips (5) following frame extension. The microneedles now protrude beyond the outer circumference.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A microprotrusion array for use in transport of a material across a biological barrier, wherein said array comprises a plurality of microprotrusions composed of a swellable polymer composition which in its dry state is hard and brittle to penetrate the stratum corneum of mammalian skin, wherein the microprotrusions are fabricated from at least one polymer selected from poly(methylvinylether/maleic acid), esters thereof and poly (methyl/vinyl ether/maleic anhydride), wherein the polymer is a cross-linked polymer, and using a cross-linker at a polymer-crosslinker ratio of 2:1.

2. The microprotrusion array of claim 1 wherein the microprotrusions can puncture the stratum corneum of mammalian skin and, in use, upon insertion into the skin, the microprotrusions swell.

3. The microprotrusion array of claim 1, wherein the array comprises a plurality of groups of microprotrusions, wherein the microprotrusions of each group differ in size and/or composition from those of each other group.

4. The microprotrusion array of claim 3, wherein the microprotrusions of a first group comprises at least one different cross-linker to the cross-linker of the microprotrusions of a second group.

5. The microprotrusion array of claim 1, wherein the microprotrusions are 1-3000 μm in height.

6. The microprotrusion array of claim 1, wherein the microprotrusions have a diameter of 50-300 μm.

7. The microprotrusion array of claim 1, wherein the polymer is selected from one of poly(methylvinylether/maleic acid) and poly(methyl/vinyl ether/maleic anhydride), cross-linked using a polyhydric alcohol.

8. The microprotrusion array of claim 1, wherein the polymer composition comprises an active agent.

9. A transdermal delivery device comprising a microprotrusion array wherein said array comprises a plurality of microprotrusions composed of a swellable polymer composition which in its dry state is hard and brittle to penetrate the stratum corneum of mammalian skin, wherein the microprotrusions are fabricated from at least one polymer selected from poly(methylvinylether/maleic acid), esters thereof and poly (methyl/vinyl ether/maleic anhydride), wherein the polymer is a cross-linked polymer and comprising a reservoir, wherein said reservoir comprises an active agent.

10. The transdermal delivery device of claim 9 wherein, on insertion of the microprotrusion array into skin, the microprotrusions are adapted to swell to form a swollen matrix and allow diffusion of the active agent stored in the reservoir or matrix through the swollen matrix, providing movement of the active agent through microprotrusions to the skin.

11. The transdermal delivery device of claim 9, wherein the movement active agent moves from the reservoir or matrix through microprotrusions to the skin of the active agent is by iontophoresis.

12. The transdermal delivery device of claim 9, wherein the microprotrusions are fabricated using a cross-linker alcohol at a polymer-crosslinker ratio of 2:1.

13. A microprotrusion array for the administration of an active agent in a reservoir to a tissue of a subject in need thereof, wherein said array comprises a plurality of microprotrusions composed of a swellable polymer composition which in its dry state is hard and brittle to penetrate which in its dry state is hard and brittle to penetrate the stratum corneum of mammalian skin, wherein the microprotrusions are fabricated from at least one polymer selected from poly(methylvinylether/maleic acid), esters thereof and poly (methyl/vinyl ether/maleic anhydride), wherein the polymer is a cross-linked polymer, said administration comprising the steps of:
applying the microprotrusion array to the skin such that the microprotrusions protrude through or into the stratum corneum,
allowing the microprotrusions to swell, and
allowing the active agent to flow from the reservoir through the microprotrusions and into the skin.

14. The microprotrusion array of claim 13, wherein the active agent is a drug, a cosmetic compound or a nutrient.

15. The microprotrusion array of claim 13, wherein the microprotrusions are fabricated using a cross-linker alcohol at a polymer-crosslinker ratio of 2:1.

16. An iontophoretic device comprising a microprotrusion array, wherein said array comprises a plurality of microprotrusions composed of a swellable polymer composition which in its dry state is hard and brittle to penetrate the stratum corneum of mammalian skin, wherein the microprotrusions are fabricated from at least one polymer selected from poly(methylvinylether/maleic acid), esters thereof and poly (methyl/vinyl ether/maleic anhydride), wherein the polymer is a cross-linked polymer, and using a cross-linker at a polymer-crosslinker ratio of 2:1.

* * * * *

UNITED STATES PATENT AND TRADEMARK OFFICE
CERTIFICATE OF CORRECTION

PATENT NO. : 9,549,746 B2  
APPLICATION NO. : 12/680118  
DATED : January 24, 2017  
INVENTOR(S) : A. David Woolfson et al.

Page 1 of 1

It is certified that error appears in the above-identified patent and that said Letters Patent is hereby corrected as shown below:

In the Claims

Column 28, Lines 8-9, Claim 13    Replace "which in its dry state is hard and brittle to penetrate which in its dry state is hard and brittle to penetrate" with -- which in its dry state is hard and brittle to penetrate --

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*